US009533082B2

(12) United States Patent
Reichenbach et al.

(10) Patent No.: US 9,533,082 B2
(45) Date of Patent: Jan. 3, 2017

(54) PUMP AND METHOD FOR MIXED FLOW BLOOD PUMPING

(71) Applicant: Thoratec Corporation, Pleasanton, CA (US)

(72) Inventors: Steven H. Reichenbach, Pleasanton, CA (US); Stephen G. Briana, Pleasanton, CA (US); William V. Hodges, Tracy, CA (US); Eric Lee, Oakland, CA (US); Yi-Ren Woo, Livermore, CA (US); Onur Dur, Milpitas, CA (US); David Gary Eldridge, Dublin, CA (US); Pieter W. C. J. le Blanc, Rancho Cordova, CA (US)

(73) Assignee: THORATEC CORPORATION, Pleasanton, CA (US)

( * ) Notice: Subject to any disclaimer, the term of this patent is extended or adjusted under 35 U.S.C. 154(b) by 77 days.

(21) Appl. No.: 14/489,041

(22) Filed: Sep. 17, 2014

(65) Prior Publication Data
US 2015/0005572 A1    Jan. 1, 2015

Related U.S. Application Data

(63) Continuation of application No. 13/650,874, filed on Oct. 12, 2012, now Pat. No. 8,864,643.
(Continued)

(51) Int. Cl.
*A61M 1/10*    (2006.01)
*A61F 2/07*    (2013.01)
(Continued)

(52) U.S. Cl.
CPC ............... *A61M 1/101* (2013.01); *A61F 2/07* (2013.01); *A61M 1/1086* (2013.01); *A61M 1/122* (2014.02);
(Continued)

(58) Field of Classification Search
CPC ...... A61M 1/10; A61M 1/1001; A61M 1/101; A61M 1/1029; A61M 1/1046; A61M 1/12; A61M 1/122; A61M 1/127
(Continued)

(56) References Cited

U.S. PATENT DOCUMENTS

| 4,082,376 A | 4/1978 | Wehde et al. |
| 4,458,366 A | 7/1984 | MacGregor |
| 4,508,535 A | 4/1985 | Joh et al. |
| 4,625,712 A | 12/1986 | Wampler |
| 4,688,998 A | 8/1987 | Olsen et al. |
| 4,704,121 A | 11/1987 | Moise |
| 4,779,614 A | 10/1988 | Moise |
| 4,817,586 A | 4/1989 | Wampler |
| 4,846,152 A | 7/1989 | Wampler et al. |

(Continued)

FOREIGN PATENT DOCUMENTS

| CA | 2 624 704 A1 | 4/2007 |
| CN | 101282748 A | 10/2008 |

(Continued)

OTHER PUBLICATIONS

Notification of Transmittal of The International Search Report and The Written Opinion of The International Searching Authority, or The Declaration; International Search Report and Written Opinion of The International Searching Authority for corresponding International Patent Application No. PCT/US2012/060071 mailed on Mar. 27, 2013, 14 pages.
(Continued)

*Primary Examiner* — Allen Porter, Jr.
(74) *Attorney, Agent, or Firm* — Kilpatrick Townsend & Stockton LLP

(57) ABSTRACT

A blood pump includes a hub having an axis of rotation and a generally cylindrical shape. The hub has an upstream end region, a central region, and a downstream end region, and the hub includes a magnetic material. Blades that are disposed on the downstream end region of the hub extend downstream of the hub.

13 Claims, 19 Drawing Sheets

Related U.S. Application Data

(60) Provisional application No. 61/547,032, filed on Oct. 13, 2011.

(51) Int. Cl.

| | |
|---|---|
| F04D 17/08 | (2006.01) |
| F04D 29/046 | (2006.01) |
| F04D 29/24 | (2006.01) |
| F04D 13/06 | (2006.01) |
| A61M 1/12 | (2006.01) |
| F04D 29/22 | (2006.01) |
| A61F 2/06 | (2013.01) |

(52) U.S. Cl.
CPC ......... *F04D 13/064* (2013.01); *F04D 13/0633* (2013.01); *F04D 17/08* (2013.01); *F04D 29/046* (2013.01); *F04D 29/0467* (2013.01); *F04D 29/242* (2013.01); *A61F 2/06* (2013.01); *A61M 2205/04* (2013.01); *A61M 2205/103* (2013.01); *F04D 29/22* (2013.01); *Y10T 29/49236* (2015.01)

(58) Field of Classification Search
USPC ..................................................... 600/16, 17
See application file for complete search history.

(56) References Cited

U.S. PATENT DOCUMENTS

| | | |
|---|---|---|
| 4,895,557 A | 1/1990 | Moise et al. |
| 4,906,229 A | 3/1990 | Wampler |
| 4,908,012 A | 3/1990 | Moise et al. |
| 4,944,722 A | 7/1990 | Carriker et al. |
| 4,957,504 A | 9/1990 | Chardack |
| 4,994,078 A | 2/1991 | Jarvik |
| 5,106,273 A | 4/1992 | Lemarquand et al. |
| 5,385,581 A | 1/1995 | Bramm et al. |
| 5,393,207 A | 2/1995 | Maher et al. |
| 5,443,503 A | 8/1995 | Yamane |
| 5,588,812 A | 12/1996 | Taylor et al. |
| 5,613,935 A | 3/1997 | Jarvik |
| 5,695,471 A | 12/1997 | Wampler |
| 5,707,218 A | 1/1998 | Maher et al. |
| 5,749,855 A | 5/1998 | Reitan |
| 5,824,070 A | 10/1998 | Jarvik |
| 5,888,242 A | 3/1999 | Antaki et al. |
| 5,904,646 A * | 5/1999 | Jarvik ............... A61M 39/0247 600/16 |
| 5,917,297 A | 6/1999 | Gerster et al. |
| 5,928,131 A | 7/1999 | Prem |
| 5,951,263 A | 9/1999 | Taylor et al. |
| 6,001,056 A | 12/1999 | Jassawalla et al. |
| 6,018,208 A | 1/2000 | Maher et al. |
| 6,050,975 A | 4/2000 | Poirier |
| 6,066,086 A | 5/2000 | Antaki et al. |
| 6,093,001 A | 7/2000 | Burgreen et al. |
| 6,123,659 A | 9/2000 | le Blanc et al. |
| 6,135,710 A | 10/2000 | Araki et al. |
| 6,146,325 A | 11/2000 | Lewis et al. |
| 6,149,683 A | 11/2000 | Lancisi et al. |
| 6,186,665 B1 | 2/2001 | Maher et al. |
| 6,227,797 B1 | 5/2001 | Watterson et al. |
| 6,227,820 B1 | 5/2001 | Jarvik |
| 6,234,772 B1 | 5/2001 | Wampler et al. |
| 6,278,251 B1 | 8/2001 | Schob |
| 6,293,901 B1 | 9/2001 | Prem |
| 6,394,769 B1 | 5/2002 | Bearnson et al. |
| 6,447,266 B2 | 9/2002 | Antaki et al. |
| 6,623,475 B1 | 9/2003 | Siess |
| 6,688,861 B2 | 2/2004 | Wampler |
| 6,692,318 B2 | 2/2004 | McBride |
| 6,991,595 B2 | 1/2006 | Burke et al. |
| 7,070,398 B2 | 7/2006 | Olsen et al. |
| 7,229,258 B2 | 6/2007 | Wood et al. |
| 7,303,553 B2 | 12/2007 | Ott |
| 7,338,521 B2 | 3/2008 | Antaki et al. |
| 7,563,225 B2 | 7/2009 | Sugiura |
| 7,575,423 B2 | 8/2009 | Wampler |
| 7,578,782 B2 | 8/2009 | Miles et al. |
| 7,682,301 B2 | 3/2010 | Wampler et al. |
| 7,699,586 B2 | 4/2010 | LaRose et al. |
| 7,699,588 B2 | 4/2010 | Mendler |
| 7,753,645 B2 | 7/2010 | Wampler et al. |
| 7,798,952 B2 | 9/2010 | Tansley et al. |
| 7,802,966 B2 | 9/2010 | Wampler et al. |
| 7,824,358 B2 | 11/2010 | Cotter et al. |
| 7,841,976 B2 | 11/2010 | McBride et al. |
| 7,850,594 B2 | 12/2010 | Sutton et al. |
| 7,861,582 B2 | 1/2011 | Miyakoshi et al. |
| 7,862,501 B2 | 1/2011 | Woodard |
| 7,927,068 B2 | 4/2011 | McBride et al. |
| 7,959,551 B2 | 6/2011 | Jarvik |
| 7,963,905 B2 | 6/2011 | Salmonsen et al. |
| 7,976,271 B2 | 7/2011 | LaRose et al. |
| 7,988,728 B2 | 8/2011 | Ayre |
| 7,993,260 B2 | 8/2011 | Bolling |
| 8,002,518 B2 | 8/2011 | Woodard et al. |
| 8,096,935 B2 | 1/2012 | Sutton et al. |
| 8,118,723 B2 | 2/2012 | Richardson et al. |
| 8,118,724 B2 | 2/2012 | Wampler et al. |
| 8,152,845 B2 | 4/2012 | Bourque |
| 8,177,703 B2 | 5/2012 | Smith et al. |
| 8,282,359 B2 | 10/2012 | Ayre et al. |
| 8,343,028 B2 | 1/2013 | Gregoric et al. |
| 8,353,686 B2 | 1/2013 | Cook |
| 8,366,381 B2 | 2/2013 | Woodard et al. |
| 8,366,599 B2 | 2/2013 | Tansley et al. |
| 8,376,707 B2 | 2/2013 | McBride et al. |
| 8,864,643 B2 | 10/2014 | Reichenbach et al. |
| 2002/0147495 A1 | 10/2002 | Petroff |
| 2002/0149200 A1 | 10/2002 | Fumioka |
| 2003/0100816 A1 | 5/2003 | Siess |
| 2004/0236420 A1 | 11/2004 | Yamane et al. |
| 2005/0004421 A1 | 1/2005 | Pacella et al. |
| 2005/0095151 A1 | 5/2005 | Wampler et al. |
| 2005/0107657 A1 | 5/2005 | Carrier et al. |
| 2005/0147512 A1 | 7/2005 | Chen et al. |
| 2005/0254976 A1 | 11/2005 | Carrier et al. |
| 2007/0078293 A1 | 4/2007 | Shambaugh et al. |
| 2007/0100196 A1 | 5/2007 | LaRose et al. |
| 2007/0156006 A1 | 7/2007 | Smith et al. |
| 2008/0269880 A1 | 10/2008 | Jarvik |
| 2009/0118567 A1 | 5/2009 | Siess |
| 2010/0069847 A1 | 3/2010 | LaRose et al. |
| 2010/0145133 A1 | 6/2010 | Bolling |
| 2010/0150749 A1 | 6/2010 | Horvath |
| 2010/0152526 A1 | 6/2010 | Pacella et al. |
| 2011/0054239 A1 | 3/2011 | Sutton et al. |
| 2011/0144413 A1 | 6/2011 | Foster |
| 2011/0152600 A1* | 6/2011 | Scott ...................... A61M 1/10 600/16 |
| 2011/0237863 A1 | 9/2011 | Ricci |
| 2011/0245582 A1 | 10/2011 | Zafirelis et al. |
| 2012/0035411 A1 | 2/2012 | LaRose et al. |
| 2012/0095281 A1 | 4/2012 | Reichenbach et al. |
| 2012/0134793 A1 | 5/2012 | Wu et al. |
| 2012/0134832 A1 | 5/2012 | Wu |
| 2012/0209057 A1 | 8/2012 | Siess et al. |
| 2012/0253103 A1 | 10/2012 | Robert |
| 2012/0310036 A1 | 12/2012 | Peters et al. |
| 2013/0225909 A1 | 8/2013 | Dormanen et al. |
| 2016/0074574 A1* | 3/2016 | Welsch ............... A61M 5/1452 604/152 |

FOREIGN PATENT DOCUMENTS

| | | |
|---|---|---|
| DE | 19854724 A1 | 5/1999 |
| DE | 102009047844 A1 | 3/2011 |
| DE | 112012004282 T5 | 7/2014 |
| EP | 0 150 320 B1 | 5/1990 |
| JP | 2009/511802 A | 3/2009 |
| KR | 2008056754 A | 6/2008 |
| WO | WO 00/43054 A2 | 7/2000 |

(56) References Cited

FOREIGN PATENT DOCUMENTS

| WO | WO 2007/040663 A1 | 4/2007 |
| WO | WO 2008/152425 A1 | 12/2008 |
| WO | WO 2013/056131 A1 | 4/2013 |

OTHER PUBLICATIONS

Restriction Requirement for U.S. Appl. No. 13/650,874 mailed on Jul. 25, 2013, 8 pages.
Non-Final Office Action for U.S. Appl. No. 13/650,874 mailed on Aug. 29, 2013, 7 pages.
Examiner-Initiated Interview Summary for U.S. Appl. No. 13/650,874 mailed on Jan. 28, 2014, 2 pages.
Non-Final Office Action for U.S. Appl. No. 13/650,874 mailed on Mar. 4, 2014, 5 pages.
Notice of Allowance for U.S. Appl. No. 13/650,874 mailed on Jun. 17, 2014, 7 pages.

* cited by examiner

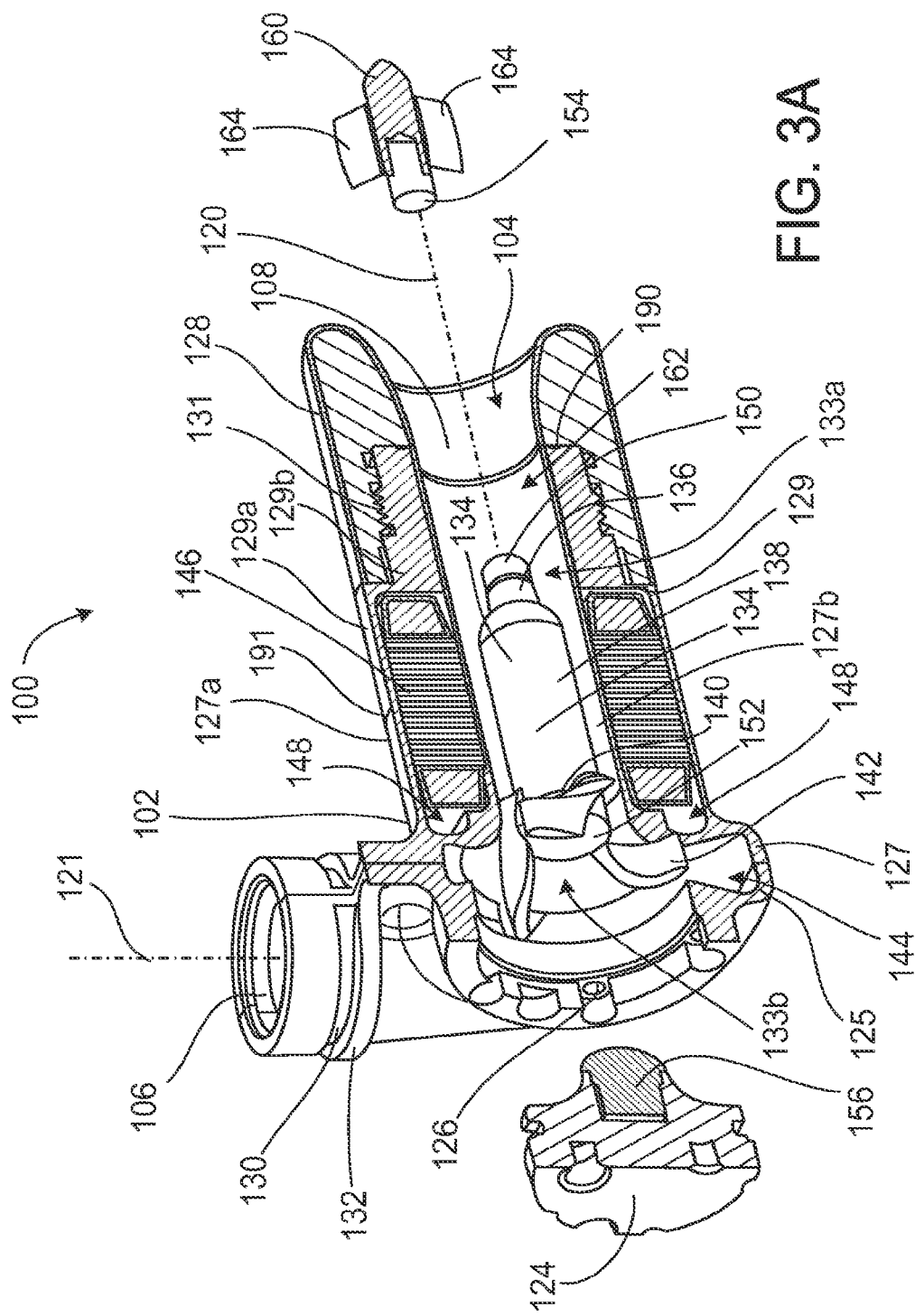

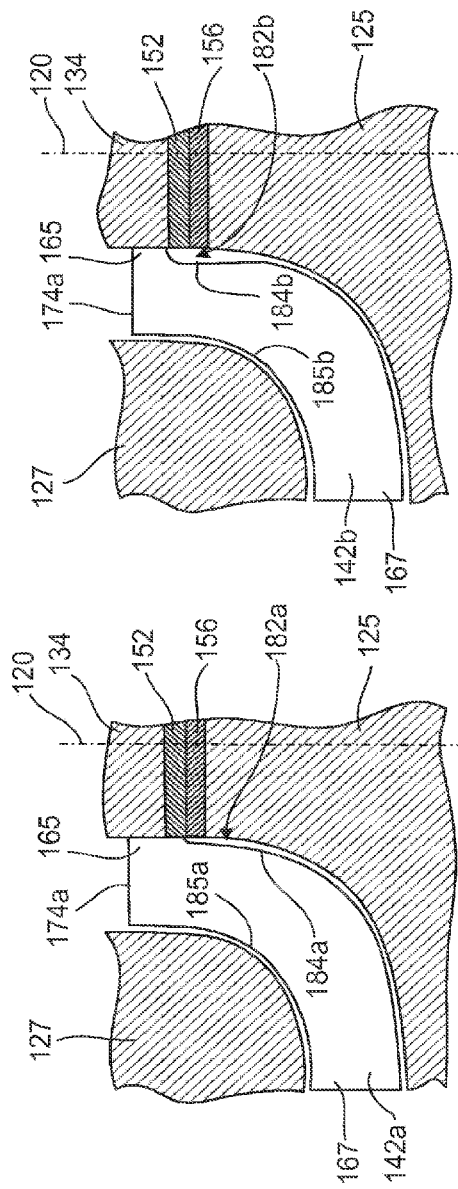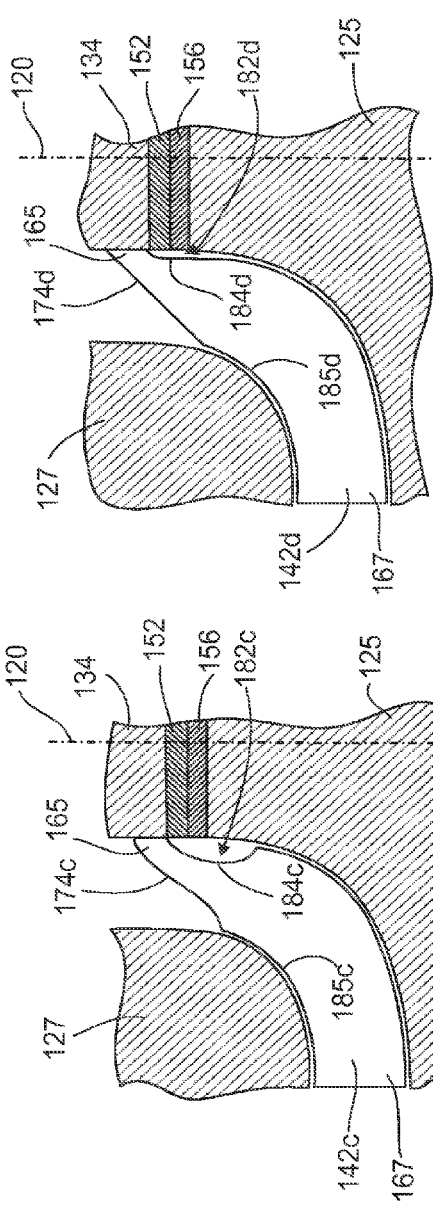

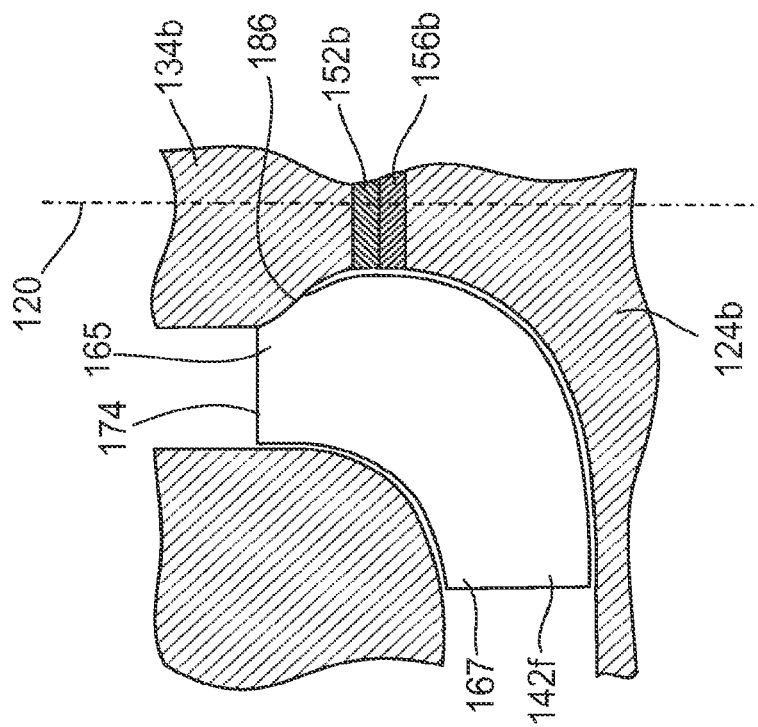
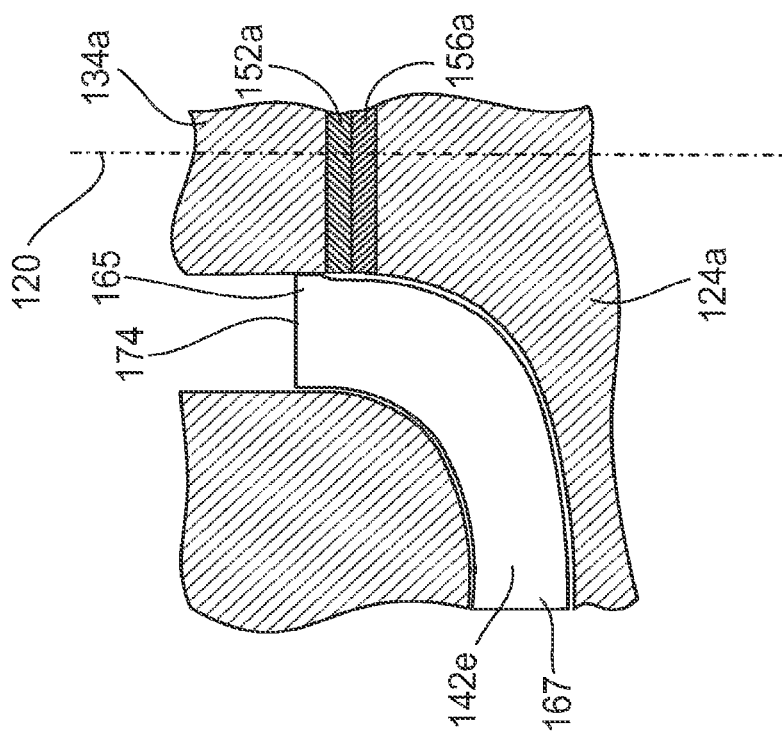

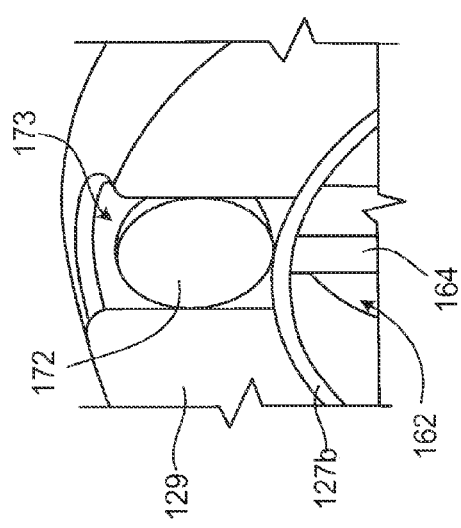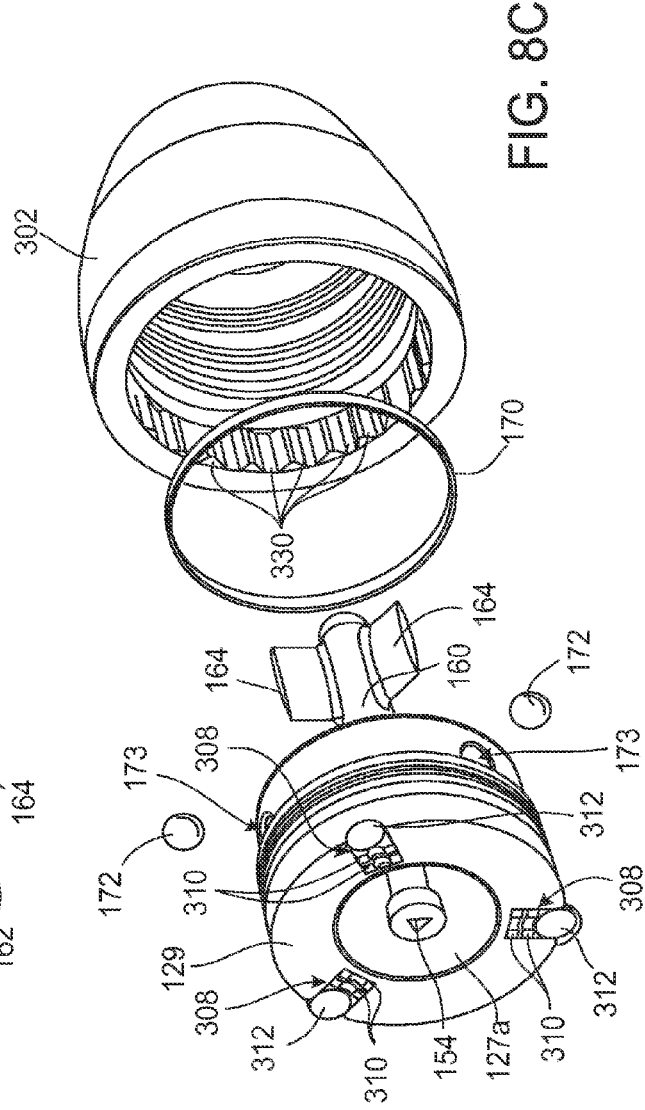

ical applications. Conventional blood pumps may cause adverse effects due to, for example, excessive shear stress.

PUMP AND METHOD FOR MIXED FLOW BLOOD PUMPING

CROSS-REFERENCES TO RELATED APPLICATIONS

The present application is a Continuation of U.S. Ser. No. 13/650,874 filed Oct. 12, 2012 (Allowed); which application claims the benefit of U.S. Provisional Appln. No. 61/547,032 filed Oct. 13, 2011; the full disclosures which are incorporated herein by reference in their entirety for all purposes.

FIELD OF THE INVENTION

This description relates to pumps, and in various respects, mixed flow blood pumping.

BACKGROUND OF THE INVENTION

Ventricular assist devices, known as VADs, are types of blood pumps used for both short-term and long-term applications where a patient's heart is incapable of providing adequate circulation. For example, a patient suffering from heart failure may use a VAD while the patient awaits a heart transplant. In another example, a patient may use a VAD while the patient recovers from heart surgery. Some heart failure patients may have the device implanted for permanent use. Thus, a VAD can supplement a weak heart or can effectively replace the natural heart's function. VADs can be implanted in the patient's body and powered by an electrical power source outside the patient's body.

BRIEF SUMMARY OF THE INVENTION

In one general aspect, a device includes a hub having an axis of rotation and a generally cylindrical shape. The hub has an upstream end region, a central region, and a downstream end region, and includes a magnetic material. Blades disposed on the downstream end region of the hub extend downstream of the hub.

In another general aspect, a blood pump includes a hub having an axis of rotation and a generally cylindrical shape, the hub having an upstream end region, a central region, and a downstream end region. The hub includes a magnetic material. The blood pump includes blades located at the downstream end region of the hub. The blades extend downstream of the hub, and each blade includes (i) an upstream portion that is located proximate the hub and is configured to add energy to the fluid having forward flow along the axis of the hub, and (ii) a downstream portion that is configured to add energy to the fluid having forward flow in a direction radially outward from the hub.

Implementations of any of the aspects can include one or more of the following features. For example, the blades extend radially outward from the hub. The blood pump includes a housing and the hub is suspended by fore and aft bearings. The central region and the upstream end region are devoid of blades. The blood pump includes a housing that defines an inlet, an outlet, and a flow path from the inlet to the outlet. A motor stator is disposed within the housing. Stator blades are disposed within the flow path proximate the upstream end region of the hub. Exactly one stator with blades is included in the flow path. The stator blades are coupled to an upstream bearing component that supports the upstream end region of the hub. A downstream bearing component that supports the downstream end region of the hub is located proximate the downstream end region of the hub. The downstream bearing component is coupled to an internal wall of the housing. The outlet is oriented off the axis of rotation of the hub. No stator blades are located downstream of the hub. The downstream end region of the hub is rotatably supported by one or more bearing components, and each blade defines a concave gap between the blade and the one or more bearing components. The housing defines the flow path to include a tapered region in which the outer diameter of the flow path narrows along the downstream direction. Each of the blades has a leading edge, and the narrowest outer diameter of the flow path along the axis of rotation occurs at an axial position along the leading edges of the blades. The narrowest outer diameter extends around the leading edges of the blades. The housing defines an asymmetrically-shaped annular volume around the axis of rotation that is in fluid communication with the outlet. An upstream wall defining the annular volume flares outward, away from the axis of rotation, and a downstream wall defining the annular volume flares inward, toward the axis of rotation.

Implementations of any of the aspects can include one or more of the following features. For example, the downstream end region of the hub includes a tapered portion in which the outer diameter of the hub decreases in the downstream direction along the axis, and the upstream portion of each blade is attached to the tapered portion. The housing defines a volute about the axis, located about the greatest outer diameter of the blades. Each of the blades has a fixed end anchored to the hub and a free end that extends into the volute. The housing includes an inner wall with a cylindrical portion with a substantially constant inner diameter, a tapered region in which the inner diameter decreases in the downstream direction. The upstream portion of each blade includes a convex surface and the downstream portion includes a concave surface, and rotation of the rotor moves the convex surface to provide the axial component of fluid flow and moves the concave surface to provide the radial component of fluid flow. The hub has a cylindrical outer surface, and the blades project from the cylindrical outer surface of the hub. The blades have a fixed end that is anchored at the maximum outer diameter of the hub. The blades have a leading edge that extends radially outward from the hub. The downstream end region of the hub includes an aft-facing surface, and the blades project from the aft-facing surface.

Implementations of any of the aspects can include one or more of the following features. For example, the blade has a fixed end disposed on the hub, and a free end that extends toward a volute. The free end extends to or into the volute. The fixed end can be formed as strut or other feature, and includes a leading edge of the blade. The fixed end includes a trailing edge that faces the volute and is generally linear. The trailing edge is chamfered or tapered. The blade has blade angles and wrap angles that vary along the length of the blade. The wrap angle is an angle indicating the extent that the blade extends circumferentially around the axis of rotation from an initial or leading point to a given point along the blade. The blade angle is an angle between the blade and the axis of rotation of the rotor that includes the blade. The blade twists along its length, resulting in wrap angles and blade angles that are different along an inner edge of the blade and along an outer edge of the blade.

Implementations of any of the aspects can include one or more of the following features. For example, the inner edge faces generally inward toward the axis of rotation of the hub. The inner edge includes a portion that faces toward the axis of rotation and a portion that faces toward an aft or downstream direction. An aft interior wall of the pump housing defines a clearance with the portion of the inner edge that faces toward the aft or downstream direction. The wrap angle is zero degrees at the beginning or leading point of the inner edge. Moving in a downstream direction, the wrap angle increases along an initial region (or most upstream region) of the inner edge. The initial region of the inner edge is approximately one quarter to one third of the length of the inner edge. The wrap angle has a decreasing rate of change in the initial region. The wrap angle remains generally constant along a central region of the inner edge of the blade. The central region is approximately the central one third of length of the inner edge. The wrap angle varies within a range of 10 degrees, or within a range of 5 degrees, or less along the central region. The wrap angle increases with an increasing rate of change along an end region, or most downstream region, of the inner edge. The end region is approximately one third of the length of the inner edge. The maximum wrap angle is approximately 100 degrees at the end of the inner edge, where the inner edge meets the trailing edge. The maximum wrap angle along the inner edge is between 85 degrees and 115 degrees, or between 90 degrees and 110 degrees. The magnitude of the increase or decrease of the rate of change of the wrap angle along the initial region and along the end region are approximately equal.

Implementations of any of the aspects can include one or more of the following features. For example, in a downstream direction, the blade angle decreases along an initial region of the inner edge, to a position approximately one third to one half of the length of the inner edge. The blade angle increases along the remainder of the blade. The blade angle at the final or trailing portion of the inner edge is equal to or greater than the blade angle at the initial or leading portion of the blade. The rate of change of the blade angle increases along substantially the entire inner edge. The rate of change of the blade angle increases at a generally constant rate. The blade angle varies by at least 30 degrees, at least 40 degrees, at least 50 degrees, or more along the length of the inner edge. The lowest value of the blade angle along the inner edge occurs at a position between approximately one third and one half of the length of the inner edge. The final blade angle along the inner edge is greater than the initial blade angle along the inner. The final blade angle and the initial blade angle can be within approximately 30 degrees, 20 degrees, or 10 degrees of each other.

Implementations of any of the aspects can include one or more of the following features. For example, the outer edge of the blade faces generally outward from the axis of rotation. The outer edge faces outward toward inner walls of the pump housing that define the flow path through the blood pump. The pump housing defines a shroud or sheath circumferentially around the outer edge, defining a desired clearance around the outer edge. The wrap angle is defined to be zero degrees at the beginning or leading point of the outer edge. In a downstream direction, the wrap angle increases at a generally constant rate along the outer edge. The final wrap angle, at the most distal or downstream point on the outer edge is between 85 degrees and 115 degrees, or between 90 degrees and 110 degrees. The final wrap angle is approximately 100 degrees. The blade angle decreases along an initial region (or most upstream region) of the outer edge, in a downstream direction. The initial region is approximately one third to one half of the length of the outer edge. The blade angle increases along an end region of the outer edge in the downstream direction. The end region is approximately the most distal or downstream one third to one half of the length of the outer edge. The rate of change of the blade angle increases at a substantially constant rate along substantially the entire outer edge. The blade angle varies no more than approximately 20 degrees, or no more than approximately 10 degrees, along the outer edge. The initial blade angle along the outer edge and the final blade angle along the outer edge are approximately equal, for example, within 10 degrees of each other, or within 5 degrees of each other. The lowest value of the blade angle along the outer edge occurs at approximately the midpoint along the length of the outer edge.

In another general aspect, a method of pumping fluid includes connecting an upstream end of a pump to a fluid source. A hub of the pump rotates to draw fluid from the fluid source to a downstream end of the pump. Blades disposed on a downstream end region of the hub are provide a mixed axial and centrifugal flow of fluid. The blades extend downstream of the downstream end region of the hub.

In another general aspect, a graft assembly for connecting a pump outlet portion to tissue includes a woven material that defines a lumen. A reinforcement component is located about the outer circumference of the woven material. A support structure for coupling the woven material to an outlet portion of the pump is molded about an end region of the woven material. The support structure includes a flange configured to be captured by a fitting.

Implementations of any of the aspects can include one or more of the following features. For example, a fitting is slidably positioned over the support structure. The fitting is configured to snap over a raised portion on an outer surface about the pump outlet such that the fitting compresses the flange of the support and forms a hermetic seal about the outlet portion. The fitting is configured to mesh with a threaded portion on an outer surface about the pump outlet such that the fitting compresses the flange of the support structure and creates a hermetic seal around the pump outlet. The reinforcement component about the outer circumference of the woven material includes a wire wrapped helically about the outer circumference of the woven material.

In another general aspect, a method of positioning an upstream stator during pump assembly includes placing the upstream stator within an inlet bore of the pump. The method includes compressing a conduit that defines the inlet bore at regions that correspond to blade locations of the upstream stator to anchor the upstream stator and provide sealing about the blades.

Implementations of any of the aspects can include one or more of the following features. For example, compressing the conduit includes placing sealing elements about the conduit at regions corresponding to blade locations of the upstream stator. An outer housing is fitted over the conduit and the sealing elements such that an inner surface of the outer housing compresses the sealing elements against an outer surface of the conduit.

In another general aspect, a blood pump assembly includes an implantable blood pump that has a motor stator with phase windings for at least three phases. Each of the phase windings has a first end and a second end, and each of the second ends is connected to a common loadable point. The blood pump assembly includes a pump controller and a percutaneous lead for connecting the blood pump to the pump controller. The percutaneous lead includes a first conductor for connecting the pump controller and the first end of a first of the phase windings, a second conductor for connecting the pump controller and the first end of a second of the phase windings, a third conductor for connecting the pump controller and the first end of a third of the phase windings, and an additional conductor for connecting the pump controller and the common loadable point. The pump controller is configured to independently control the current in the first, second, third, and additional conductors.

In another general aspect, a blood pump assembly includes an implantable blood pump and a power lead connected to the blood pump that encloses at least three conductors. The power lead includes a mating region that includes three connectors arranged in a triangular pattern. Each of the conductors terminates at one of the connectors. The blood pump assembly includes a power connector that includes a mating region for connecting with the power lead mating region. The power connector mating region includes three connectors each arranged to receive one of the power lead connectors. The blood pump is configured to be powered by the power lead when the power lead and the power connector are connected in any one of three mating positions.

Implementations of any of the aspects can include one or more of the following features. For example, the power lead connectors include female connectors and power end connectors include male connectors. The power lead connected to the blood pump encloses four conductors, and the fourth conductor terminates at a fourth connector of the mounting region located generally at the center of the triangular pattern. The power end connector mating region includes a fourth connector for receiving the fourth power lead connector.

Various aspects of the disclosure are directed to a blood pump assembly comprising any of the features described above. Implementations can include some or all of the aspects and features described above, in any combination or sub-combination. Various aspects of the disclosure are directed to a method of using a blood pump assembly comprising any of the features described above to pump blood and provide a mix of axial and centrifugal flow. One can appreciate that features disclosed for one implementation can be combined with other features present in a different implementation and that combinations of features are not limited only to the configurations as illustrated in the disclosed implementations.

The details of one or more implementations are set forth in the accompanying drawings and the description below. Other features will be apparent from the description and drawings, and from the claims.

BRIEF DESCRIPTION OF THE DRAWINGS

FIG. 3A is an exploded cutaway view of the blood pump.

FIGS. 6A-6D are meridional views of alternative blades for the hub.

FIGS. 7A-7B are meridional views of alternative blades and alternative bearing components for the hub.

FIG. 8B is a cutaway perspective view of an upstream stator and a housing of the blood pump of FIG. 8A.

FIG. 8C is an exploded view of the inlet end of the blood pump of FIG. 8A.

The details of one or more implementations are set forth in the accompanying drawings and the description below. Other features will be apparent from the description and drawings, and from the claims.

DETAILED DESCRIPTION OF THE INVENTION

Figure 1:
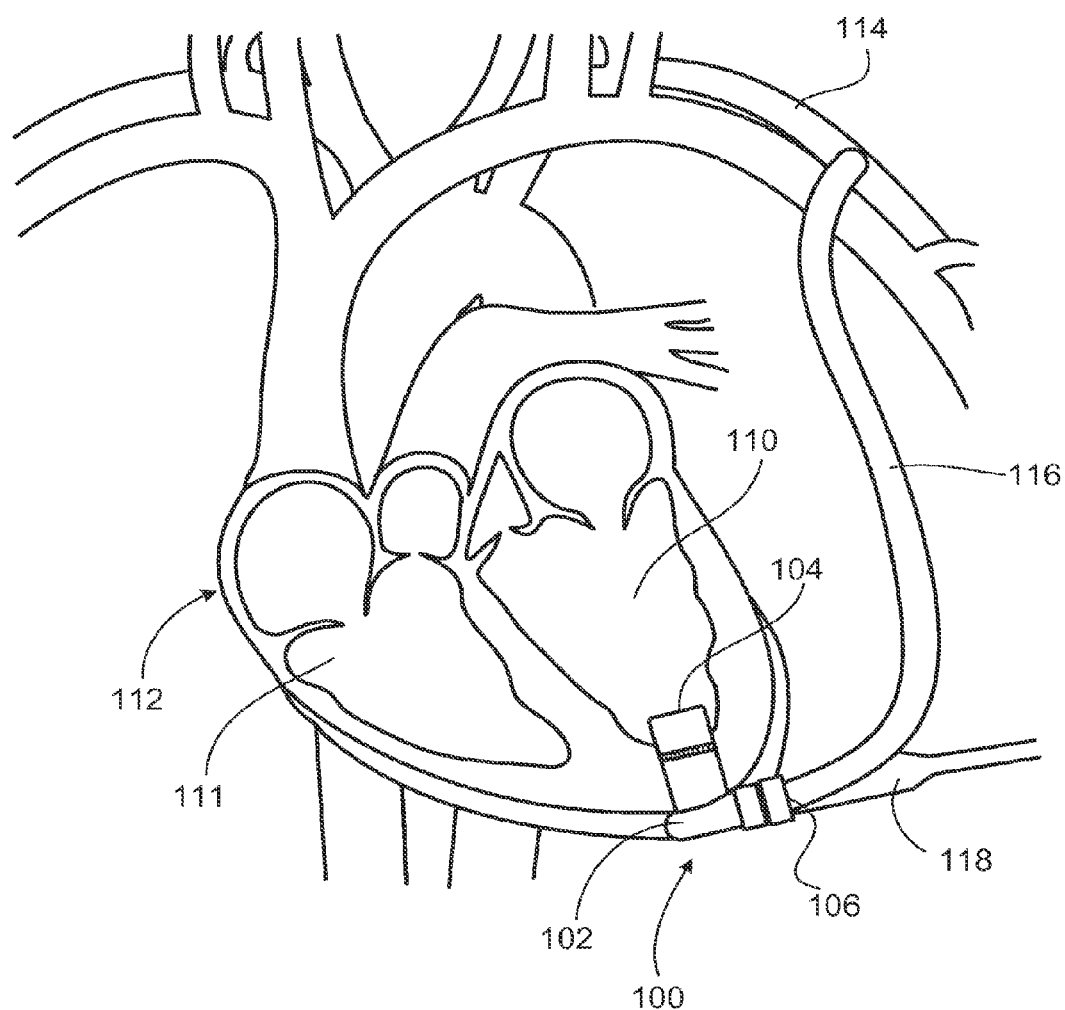
FIG. 1 illustrates a blood pump assembly implanted at a heart.

Referring to FIG. 1, an example blood pump 100 can be implanted in a patient's body to supplement, or in some cases replace, the natural pumping function of a heart 112. The blood pump 100 includes a housing 102 defining an inlet 104, an outlet 106, and an inner flow path between the inlet 104 and the outlet 106. A rotating hub (not shown) containing a magnetic material is positioned in the flow path within the housing 102 and includes a plurality of blades that provide mixed axial and centrifugal flow of fluid through the flow path.

In use, the inlet 104 can be connected, for example, to a left ventricle 110 of the heart 112 and the outlet 106 can be connected, for example, to the subclavian artery 114 via a conduit 116. Additionally, the blood pump 100 can connect to a percutaneous lead 118 that encloses a plurality of conductors, as described further below, for receiving electrical energy from a controller (not shown) that can be located outside of the patient's body. The blood pump 100 can also be implanted such that the inlet 104 receives blood from a right ventricle 111 of the heart 112 and supplies blood to, for example, a pulmonary artery.

In various implementations, the blood pump 100 is commonly configured to provide partial support or full support to a left ventricle 110 or a right ventricle 111. In various implementations, the blood pump 100 is configured for biventricular support alone, or with a second blood pump 100 or a blood pump of another type. The blood pump 100 is designed to provide general mechanical circulatory support and thus can supplement either systemic or pulmonary support. For example, the blood pump 100 can also be used to move blood from the left or right atrium or an arterial or venous vessel or any other vasculature to a different target vasculature that may include any arterial or venous vessel or organ.

The pump 100 can include other features such as those described in U.S. Provisional Application Ser. No. 61/392, 811 filed Oct. 13, 2010, and titled "Pumping Blood," U.S. Provisional Application Ser. No. 61/393,241 filed Oct. 14, 2010, and titled "Pumping Blood," and U.S. application Ser. No. 13/273,185 filed Oct. 13, 2011, and titled "Pumping Blood," the entire contents of which are incorporated herein by reference.

Figure 2:
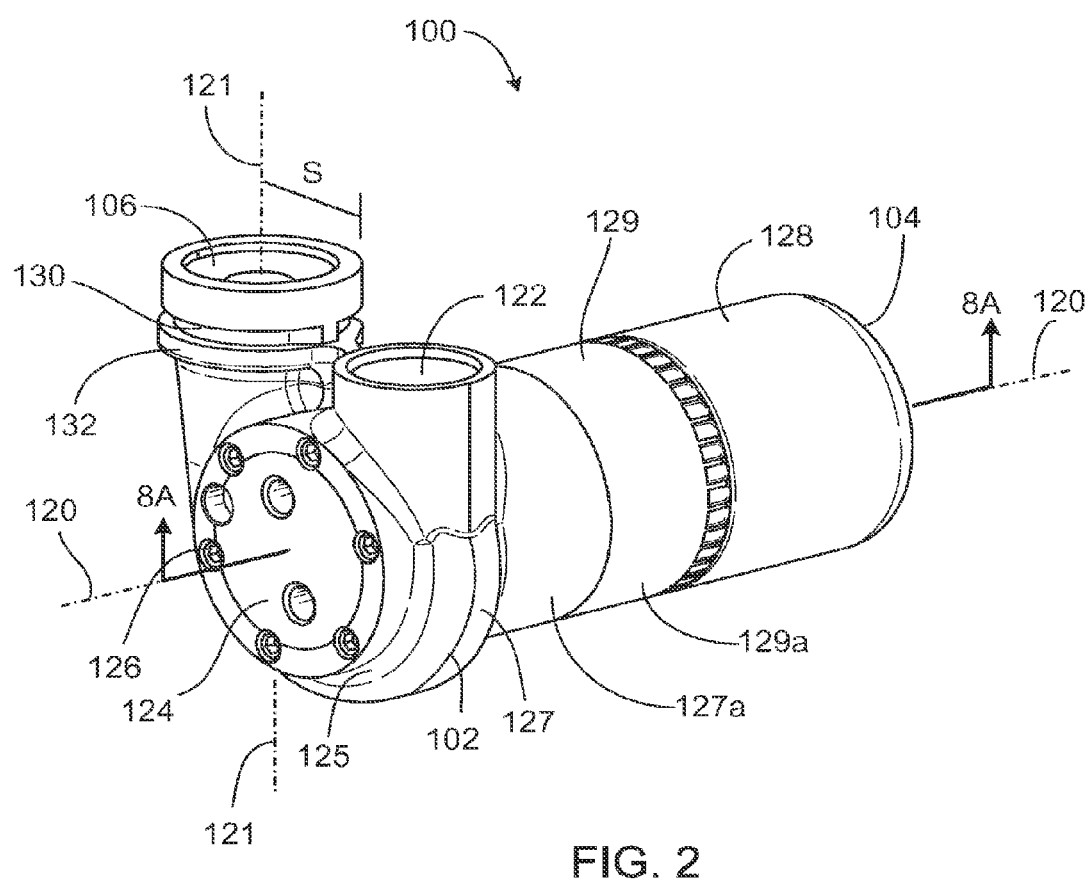
FIG. 2 is a perspective view of a blood pump of the blood pump assembly.
Figure 3B:
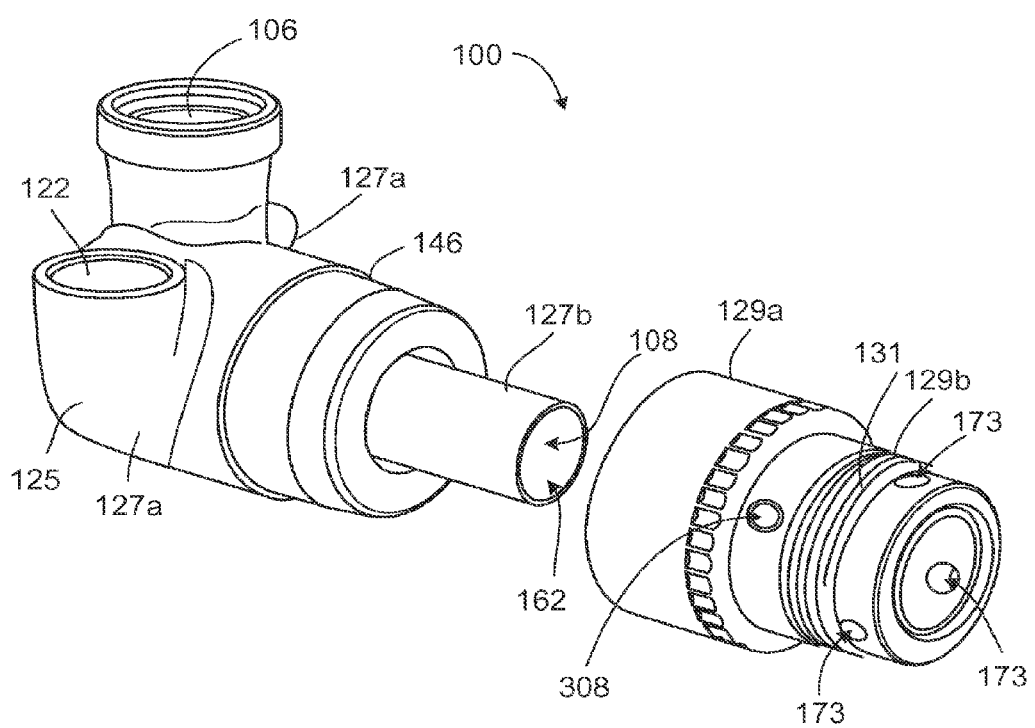
FIG. 3B is an exploded perspective view of various components of the blood pump.
Figure 4:
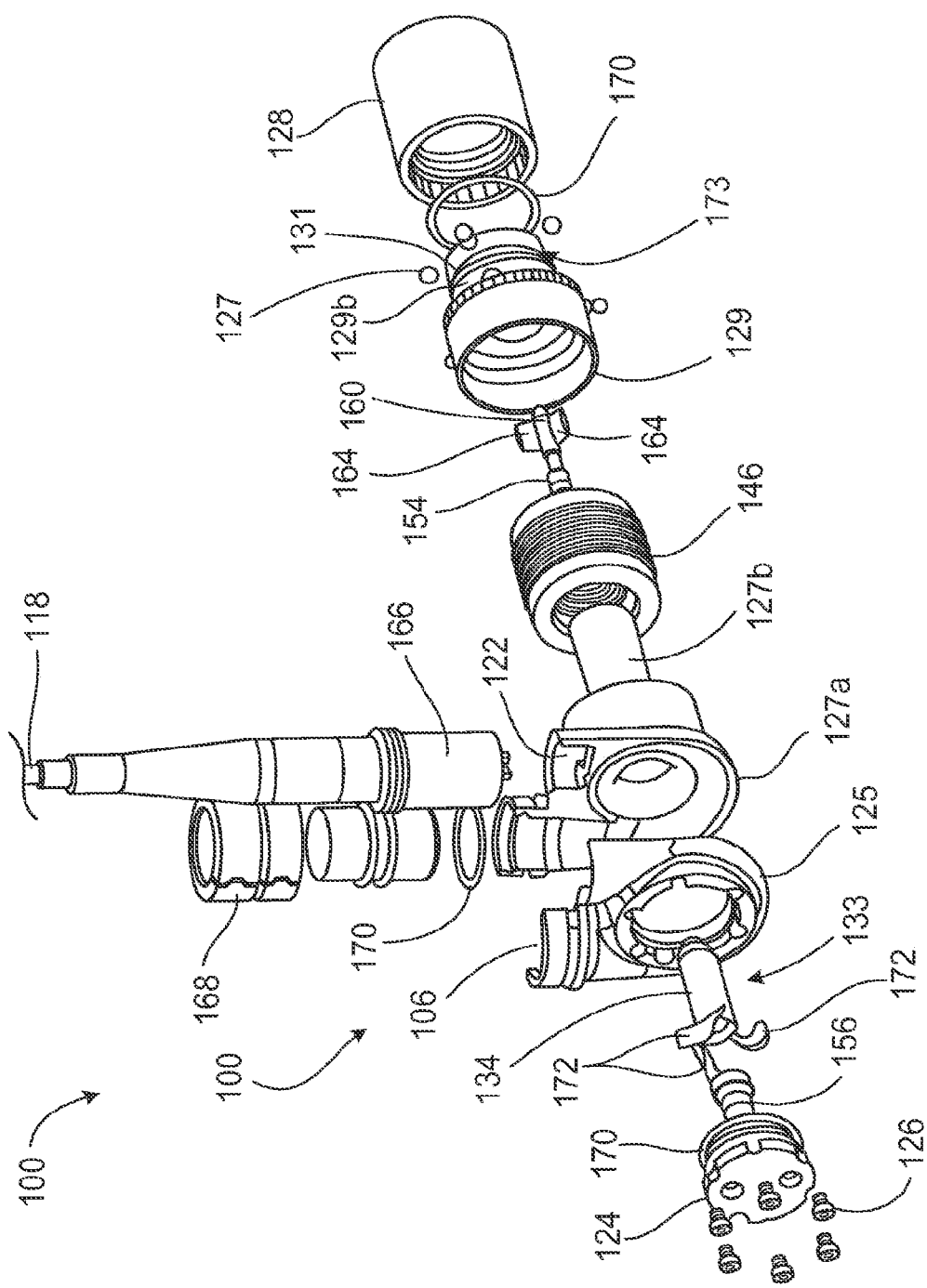
FIG. 4 is an exploded view of the blood pump.

FIGS. 2-4 illustrate the physical structure of the blood pump 100 from different perspectives. FIG. 2 illustrates the external structure of the blood pump 100. The blood pump 100 has a housing 102 that can be made of titanium or another biocompatible material and can be metal or non-metal. On the interior and exterior of the housing 102, all of or portions of metallic surfaces that come in contact with fluid can be subject to surface treatments. For example, the surface can be textured, sintered, beaded, or the like to promote the formation of a thin biological coating such as endothelial growth to discourage thrombogenesis.

The housing 102 includes a downstream component 125, a body component 127, a stator cover 129, and an inlet cap 128. Together, the downstream component 125 and the body component 127 define the outlet 106 and a port 122 that connects to the percutaneous lead 118 (shown in FIG. 1). The downstream component 125 and the body component 127 also define an annular channel 144. The downstream component 125 includes a removable back plate or plug 124, which can be secured over an opening in the downstream component 125 by screws 126. The motor stator 146 is disposed within the housing 102, which also defines the blood flow path 108. The body component 127 and the downstream component 125 of the housing 102 together define the outlet 106 of the blood pump 100 at an orientation off the inlet axis 120. For example, an outlet axis 121 defined centrally through the outlet 106 is oriented generally orthogonal to the inlet axis 120. As shown in FIG. 2, the outlet axis 121 is also laterally spaced from the inlet axis 120 by a distance, S, such that the axes 120, 121 do not intersect.

The back plate 124 and configuration of the outlet 106 advantageously provide improved access to the downstream pump components. For example, the back plate 124 improves ease of installing components within the housing 102 during manufacturing and provides an ability to vary tolerances or fine adjustment of parts internal to the blood pump 100. The outlet 106 may include features such as threads or other mechanism to enhance interchangeability with different outflow conduits (not shown). In some implementations, outflow conduits may vary in size, shape, or material depending on the anatomical characteristics and the tissue composition of a target vasculature, and how the outflow conduit is designed to couple with the target vasculature. Ease of interchangeability promotes ease of use in an operation room and increases versatility of the blood pump 100. The port 122 is designed to receive a percutaneous lead that is intended to provide power and/or control signals to operate the blood pump 100.

In combination with FIG. 3B, the body component 127, the stator cover 129, and the inlet cap 128 are further described below. The body component 127 includes an outer portion 127a that couples with the downstream component 125 or cover and an inner tubular portion 127b with an inner surface that defines an inlet bore 162 where a rotor 133 and an upstream stator 160 are located.

A motor stator 146 for driving the rotor 133 (FIG. 3A) resides about the outer surface of the inner tubular portion 127b between the outer portion 127a of the body component 127 and the inner tubular portion 127b of the body component 127. The motor stator 146 is partially covered by the outer portion 127a of the body component 127 and the stator cover 129 as shown. The stator cover 129 has a visible portion 129a that partially covers the motor stator 146 and further wraps over the inner tubular portion 127b. A hidden portion 129b of the stator cover 129 receives the inlet cap 128. In other words, the stator cover 129 wraps around part of the motor stator 146 and around the inner tubular portion 127b. The inlet cap 128 is secured directly over the hidden portion 129b of the stator cover 129, which can include threads 131 and additional locking features located inside radial holes 308. The hidden portion 129b of the stator cover 129 further includes plug holes 173 that are intended to receive a press-fit feature such as a spherical structure (not shown) that directly presses over the wall of the inner tubular portion 127b in securing stator blades 164 that functions to suspend and hold the rotor 133 in place (see FIG. 3A). There is no seam, gap, hole, or the like in the blood flow path 108 defined by the inner tubular portion 127b from the upstream end to the downstream end along the blood flow path 108. Both the stator blades 164 and the rotor 133 are disposed within the inlet bore 162 and within the flow path 108 proximate an upstream end region 136 of the hub 134.

As shown in FIG. 3A, which illustrates a cross-sectional view of the pump 100, the body component 127 and the stator cover 129 are joined by circumferential welds 190 between the inner tubular portion 127b and the hidden portion 129b of the stator cover 129, and by circumferential welds 191 between the outer portion 127a of the body component 127 and the visible portion 129a of the stator cover 129 to define an annular compartment 148. The motor stator 146 is disposed within the compartment 148 partially covered by the outer portion 127a of the body component 127 and partially covered by the visible portion 129a of the stator cover 129. The inner surface of the inlet cap 128 joins seamlessly with the inner tube portion 127b at the upstream end of the pump to define the inlet 104. Inlet caps of different shapes, materials, and textures can be selected for use at particular implantation locations.

As shown in FIG. 3A and in FIG. 4 the rotor 133 is mechanically suspended within the housing 102 by bearings at an upstream end region 133a and a downstream end region 133b. At the upstream end region 133a, the rotor 133 includes a fore or upstream bearing component 150 that rotates relative to a stator bearing component 154 coupled to the upstream stator 160. The implementation as shown illustrates the ball component 150 on the rotor 133 and the cup component 154 on the stator 160, but the reverse is also possible. Different materials can be selected for the ball and cup components of the bearing assembly based on the material hardness and the wear of the material upon use. For instance, materials including, but not limited to, precious stone (e.g., sapphire, ruby, corundum, diamond, cubic zirconia, etc.) and ceramics can be used. The upstream stator blades 160 and the stator bearing component 154 can be formed as an integral component or as separate components. At the downstream end region 133b, the rotor 133 includes an aft or downstream bearing component 152 that rotates relative to a housing bearing component 156. In some implementations, the ball and cup like components, shown with the ball component 150 on the back plate 124 and the cup component 154 on the downstream portion 133b of the rotor 133, can be reversed. In some implementations, the housing bearing component 156 is directly coupled to the housing 102, for example, on the back plate 124.

The shapes and sizes of the bearing components 150, 152, 154, 156 can be selected to suit a particular implementation. For example, the housing bearing component 156 can include a generally convex surface, and the downstream bearing component 152 can include a matching concave surface. The stator bearing component 154 can include a generally concave surface, and the upstream bearing component 150 can include a matching convex surface. In use within a fluid environment, a small gap (e.g., approximately between about 0.0001 inches to about 0.0006 inches) can be maintained between proximate bearing components (e.g., between the bearing components 150, 154 and between the bearing components 152, 156). In some implementations the total gap size between the upstream and downstream bearing gaps is approximately 0.0002 inches.

Returning to FIG. 3A, the blood pump 100 is configured to provide partial or full support to a patient's circulatory system. The blood pump 100 includes a rotor 133 that moves blood along a flow path 108 from the inlet 104 to the outlet 106. The rotor 133 includes a hub 134 that has an axis of rotation, such as an inlet axis 120, and a generally cylindrical shape along the length of the rotor 133. The hub 134 has an upstream end region 136, a central region 138, and a downstream end region 140. The hub 134 includes a magnetic material (not shown). The blood pump 100 includes blades 142 for promoting flow. The blades 142 are positioned along a blade region of the hub 134 of the rotor 133.

In some implementations, blades 142 are disposed on the downstream end region 140 of the hub 134, e.g., located distally past a midpoint of the hub 134 or downstream of the central region 138 of the hub 134. In the illustrated implementation, blades 142 extend downstream of the body of the hub 134 past the downstream end region 140 of the hub 134. In various implementations, including the one as shown, the upstream end region 136 and the central region 138 of the hub 134 are devoid of any blades. In other implementations, the blades 142 may begin at or slightly distal of the midpoint of the hub 134 and extend along all or a part of the end region 136 and/or central region 138 while the upstream end region 136 is devoid of any blades. Incorporating a radial flow configuration allows the elimination of an aft stator, thus allowing surface area reduction as well as avoiding additional higher shear regions that typically occur at the stator blade leading edges.

In the implementation illustrated, the rotor 133 includes three blades 142 spaced approximately 60 degrees apart. Other implementations can include, for example, as few as one blade 142 or up to ten blades 142 or more. The blades 142 are circumferentially spaced apart at the same axial location, in this example, the spacing is equal between all blades 142. Each blade 142 has approximately the same length and geometry or curvature. In various implementations, a blade can shape like a "J" but with the bottom portion of the "J" twisted at an angle. For instance, this wrap angle can range approximately from about 60 degrees to about 270 degrees. Generally each blade 142 can have a constant width along the entire length of the blade 142, or have a varying with along its length. For example, along the length of the "J", the width of the blade can increase gradually to a greater width at the bottom of the "J" portion relative to the vertical portion of the "J". Furthermore, the thickness of the blade 142 can also remain constant or vary along the length of the blades 142. The implementation as shown illustrates that each blade 142 has a curvature that extends downstream and flares radially outward (consequent of the "J" shape and wrap angle) such that a free end 167 of the blade 142 is at a radial distance much larger than the width of the blade 142. The configuration of blades 142 illustrated can provide both axial and centrifugal flow. In contrast, a blade that extends downstream where the curvature does not flare radially outward, or simply follows the circumference of the rotor 133, would generate an axial flow component and much less of a centrifugal component.

As described in more detail below, the blades 142 draw fluid through the inlet 104, generating a generally axial flow along the inlet axis 120. A portion of each blade 142 extends into an annular channel 144 defined by a housing 102 of the blood pump 100. The volute or annular channel 144 is located about the inlet axis 120 and is in fluid communication with the outlet 106. The volute or annular channel 144 can have a spiral shape, and can have a cross-sectional area that increases along the flow path to assist in converting kinetic energy to pressure at the outlet 106. As the hub 134 rotates, the blades 142 produce a generally centrifugal flow within the volute or annular channel 144, causing fluid to flow through the outlet 106.

In general, the blades 142 move fluid within the housing 102 to impart energy to the fluid, in order to create a desired head pressure at the outlet 106. The blades 142 act to maintain or increase pressure at the outlet 106 by imparting kinetic energy. While velocity of the fluid may be different at various localized regions within the flow path 108, the effect of the blades 142 is to maintain or increase pressure at the outlet 106, as well as to promote fluid flow through the outlet 106. In some implementations, the axial velocity of fluid through the pump 100 is substantially constant over the hub 134.

Rotation of the rotor 133 is driven by the motor stator 146 located about the hub 134. Electrical current flows through wire windings of the motor stator 146 to produce varying magnetic fields. The magnetic fields interact with the magnetic material of the hub 134 to cause rotation of the rotor 133. Wiring used in the motor stator 146 can be any highly conductive material, including but not limited to copper, silver, or other materials. The motor stator 146 is entirely hermetically sealed in the pump housing 102, just like the magnetic material is hermetically encapsulated and sealed in or on the hub 134. The magnetic material can be located anywhere in or on the hub 134 and may be present as one or multiple parts. The rotor material may also be fabricated from magnetic materials. In some implementations, the motor stator 146 includes three wire windings that are positioned, for example, 120 degrees apart to form a three-phase motor stator. Other winding configurations can alternatively be used, including configurations that include more than or fewer than three phases. One will appreciate from the description herein that other mechanisms may be employed to drive the rotor 133.

Figure 5A:
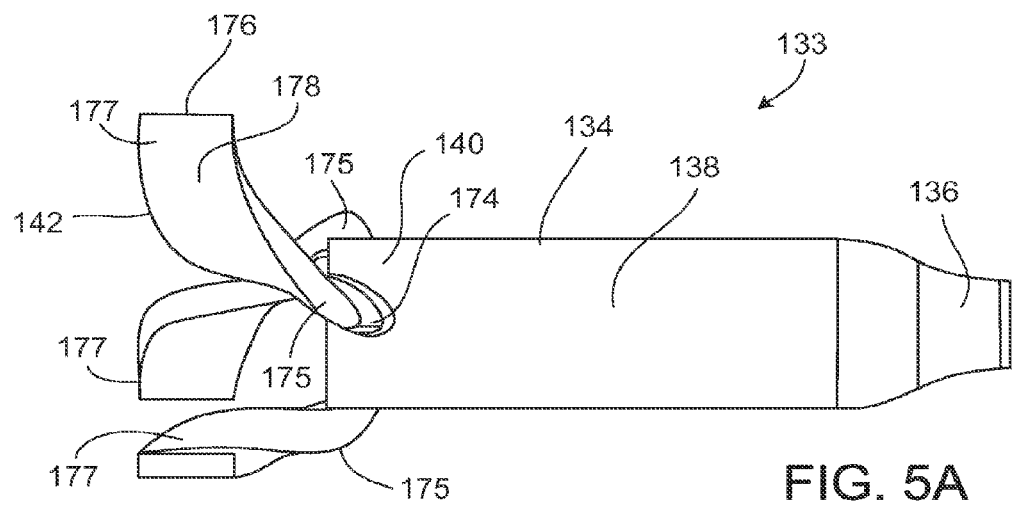
FIG. 5A is a perspective view of a hub of the blood pump.
Figure 5B:
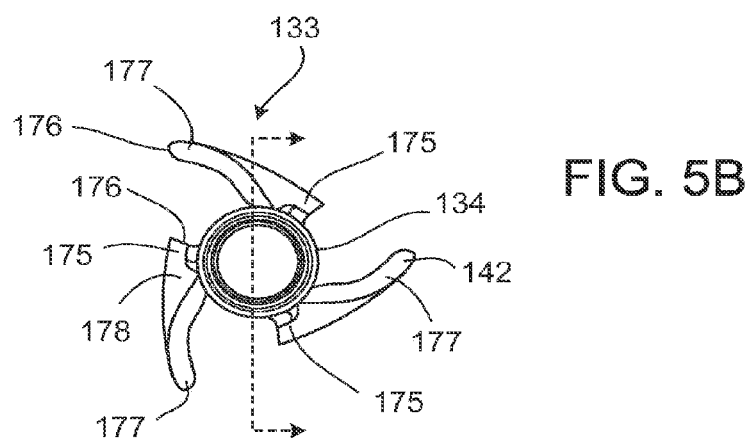
FIG. 5B is an axial view of the hub.
Figure 5C:
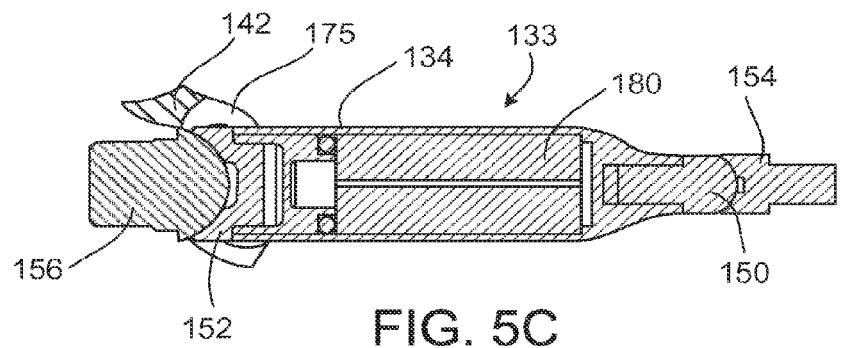
FIG. 5C is a cross-sectional view of the hub taken at line 5C-5C of FIG. 5B.
Figure 8A:
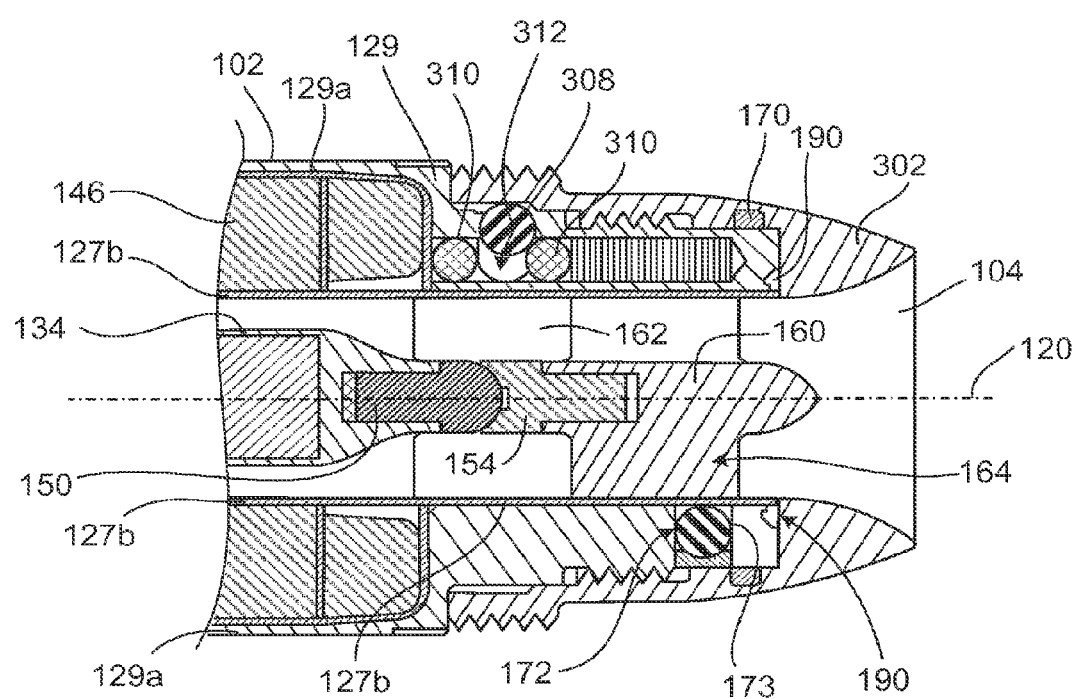
FIG. 8A is a cross-sectional view of an inlet end of a blood pump taken at line 8A-8A of FIG. 2.

Referring to FIGS. 5A-5C, the blades 142 attach to the downstream end region 140 of the hub 134. Each blade 142 includes a leading edge 174, a trailing edge 176, and a body 178. The body 178 of each blade 142 extends downstream of the hub 134 and extends radially outward within the annular channel 144 (FIG. 3). The blades 142 are sized and shaped to impart kinetic energy to the fluid flow. For example, as the rotor 133 rotates, the blade 142 draws the fluid and moves the fluid along the length of the blade 142. As each blade 142 curves downstream, the fluid is moved in the direction from upstream to downstream. Since the blade 142 also extends and flares radially outward, the rotational component of velocity is further increased downstream. The exemplary blade is shaped and dimensioned to optimize flow from the inlet to the outlet while creating a desired head pressure.

Viewing an individual blade 142 in detail, an upstream portion 175 of the blade 142 proximate the hub 134 generally provides an axial component of fluid flow where the blade portion 175 generally extends in an axial direction downstream, and a downstream portion 177 of the blade 142, positioned in the annular channel 144, provides a radial component of fluid flow where the blade portion 177 generally extends in a radial direction away from the hub 134. A configuration of blades 142 on the hub 134 that creates both axial and radial (centrifugal) flow along the flow path 108 generally limits undesired secondary flow paths within the flow path 108 and can allow, for example, direct washing of many or all surfaces within the blood pump 100. The desired rotation of the hub 134 is produced by the interaction of magnetic fields generated by the motor stator 146 with a magnetic material 180 hermetically enclosed within the hub 134.

FIGS. 6A-6D illustrate various alternative blade, or vane, configurations for use with the pump assembly described above. Alternative blades 142a-142d can be located near the downstream end region 140 of the hub 134. Each configuration extends downstream past an end of the hub 134 which is defined by the downstream bearing assembly components 152, 156. The illustrations show that each blade 142a-142d extends from, or cantilevers off, the rotor 133. One end 165 of each blade 142a-142d is anchored to the hub 134 and the remainder of the blade 142a-142d extends into the flow path, for example, with a free end 167 extending to, near, or into a volute. Each blade 142a-142d extends from the hub 134 from a location over the upstream end of the downstream bearing component 152. In other implementations, the blade 142a-142d extends from or cantilevers off other portions of the rotor, such as an edge of the hub 134 or a downstream end of the bearing component 152 on the rotor 133. The blades 142a-142d can have different leading edge shapes and can define gaps of different sizes and shapes, relative to the hub 134 and the axis of rotation near the downstream bearing components 152, 156. The different blades 142a-142d can be designed to facilitate washing of gaps between and/or around the downstream bearing components 152, 156. The shape of the blades 142 may be designed to reduce energy dissipation in the fluid. Additionally, or alternatively, the configuration of blades 142 can be selected to reduce localized mechanical stress at the downstream end region 140 where the blades 142 attach to the hub 134, or to provide modified flow paths over the leading edge 174.

As shown in FIG. 6A, a blade 142a has a leading edge 174a that is substantially orthogonal to the inlet axis 120. A generally small and constant gap 182a ranging from approximately 0.0001 inch to approximately 0.007 inch is maintained along the entire length of the blade 142a on both sides between an outer edge 185a of blade 142a and an inner surface of the housing 102 (e.g., as defined by body component 127) and an inner edge 184a of blade 142a and another inner surface of the housing 102 (e.g., as defined by downstream component 125), where the downstream bearing component 156 is located. Some implementations have about a 0.003 inch gap clearance. Efficiency of the blades moving fluids generally improves as the gap distance decreases between blades and housing inner walls.

FIG. 6B shows a blade 142b having a similar configuration as in FIG. 6A except for a gap 182b, for example a concave gap, created downstream of the hub 134 between the inner edge 184b of the blade 142b and the downstream bearing components 152, 156. The gap 182 is defined by a cutaway portion of the blade 142b adjacent the downstream bearing assembly components 152, 156. The gap 182b leads to increased blood flow in the void between the blade 142b and the bearing assembly components 152, 156, which promotes washing of and heat transfer from surfaces of the bearing components. The gap 182b is created by cutting an area from the blade 142b in a gradually curving manner resulting in a curvature on the blade 142b having a smaller radius that continues to a larger radius moving downstream away from the bearing assembly. The largest distance in this gap 182b ranges from approximately 0.010 inches to approximately 0.040 inches and gradually decreases to a similar range of gap distances as disclosed in FIG. 6A downstream a length of the blade 142b.

FIGS. 6C-6D illustrate other modifications to the upstream portion of the blades. In FIG. 6C, a blade 142c is supported by a strut-like region that provides the leading edge 174c. The resulting cutaway portions define a gap 182c with a distance, for example, ranging from approximately 0.02 inches to approximately 0.06 inches, between the inner edge of the blade 184c and the downstream bearing components 152, 156.

In FIG. 6D, a blade 142d includes a cutaway portion that defines a gap 182d with a distance, for example, ranging from approximately 0.010 inches to approximately 0.040 inches, at its maximum, between the inner edge of the blade 184d and the downstream bearing components 152, 156. The gap 182d is created similarly to the one shown in FIG. 6B with a gradually changing curvature except that the starting radius of the curve near the bearing assembly is larger than the one in FIG. 6B and that the curve terminates slightly more upstream along the length of the blade. The blade 142d includes a swept leading edge 174d relative to the incoming flow that is generally parallel to the inlet axis 120. In some implementations, a swept leading edge extends obliquely relative to the inlet axis 120. Straight leading edges may also be employed. The sweep angle of the leading edge may be used to control the flow acceleration and consequent shear in the region of the leading edge.

The cutaway angle at the leading edges 174c, 174d of the blades 142c and 142d can help to increase performance of the pump by reducing flow separation where the leading edge meets the fluid. An angled leading edge also reduces shear forces. As shown in FIGS. 6C and 6D and described above, the leading edge of the blade can take the form of a strut cantilevering off the downstream edge of the hub 134 at the bearing component 152 and extending downstream to form wide blades for moving fluid.

The various blade configurations described above are merely exemplary in nature and one skilled in the art can appreciate that the leading edge of the blade 142 can take on any shape/curvature, including but not limited to, straight orthogonal from the axis of rotation, straight at an angle from the axis of rotation, and having one or more curves extending in a downstream direction from the axis of rotation. Several of these designs alter the vane leading edge or cutaway portions of the blade to accommodate bearing washing, modify the flow over the vane leading edges or to reduce localized stresses in the structure.

FIGS. 6A-6D illustrate several approaches for enhancing washing between the rotating hub and bearing assembly and the blade or vane. The designs have an increased gap that allows additional washing in this gap region as well as eliminates stress risers where the vane joins the rotor hub 134. In the example of FIG. 6C, a strut extending from the rotor hub 134 supports the blade positioned downstream. As mentioned previously, the general downstream position blade/vanes allow radial, mixed, or hybrid hydraulic configurations. Similarly, a gap can be created between the inner edge of the blade 142 and the bearing assembly by forming the inner edges of the blades with curves of varying or constant curvatures, which promotes flow at the inner edge of the blades to prevent thrombus formation and washing the bearing components.

Referring to FIGS. 7A and 7B, alternative downstream bearing components having different diameters can be used. In FIG. 7A, the diameter of downstream bearing components 152a, 156a can be substantially equal to the diameter of a hub 134a. Alternately in FIG. 7B, a diameter of downstream bearing components 152b, 156b can be smaller than a diameter of a corresponding hub 134b. A trailing portion 186 of the hub 134b includes an axial taper directing downstream and toward the axis of rotation that terminates at a similar diameter as the bearing components 152b, 156b. The remaining downstream portion of the blade 142 curves gradually and radially outwardly towards the free end 167 of the blade 142 along the inner surface of the pump housing 102 (e.g., defined by the downstream component). Alternatively, the diameter of downstream bearing components can be larger than that of a hub. When a hub is attached to bearing components with a smaller or larger diameter, the hub can include a trailing portion that converges or diverges, respectively, to match the diameter of the bearing components and curvature as defined by the inner surface of the pump housing. The shape of the blade 142 can vary to conform to the shape of the trailing portion of the hub, as shown in FIG. 7B. The design of the downstream bearing assembly size can be modified in combination with the vane/blade design to facilitate the hydraulic design to obtain the desired flow characteristics. As such, a larger or smaller bearing (relative to the hub diameter and/or the upstream bearing diameter) can be desirable under different designs.

Referring to FIGS. 4 and 8A-8C, during assembly of the pump 100, the upstream stator 160 is positioned within the inlet bore 162. To secure the upstream stator 160, the tubular portion 127b or conduit, which is part of the inner wall of the housing that defines the inlet bore 162, is compressed at regions that correspond to blade locations of the upstream stator 160. Compression of the tubular portion 127b is achieved by inserting sealing elements 172 into plug holes 173 defined through the stator cover 129 and engaging the sealing elements with the tubular portion 127b. Each sealing element 172 is preferably of spherical or hemispherical shape, or an object that can both create a seal with no gap between the edge of the sealing element 172 and a circumferential wall of the plug hole and a force exerted against the stator blade 164 or other portions of the upstream stator 160 to secure the stator assembly in place.

The positions of the plug holes 173 correspond to locations of the stator blades 164. For example, the plug holes 173 are defined over regions of the tubular portion 127b that engage the ends of the stator blades 164 (FIG. 8B). An inlet cap, such as inlet cap 128b, is threaded over the stator cover 129. The sealing elements 172 are press-fit into the plug holes 173. Friction between the sealing elements 172 and the walls of the plug holes 173 helps secure the sealing elements against the tubular portion 127b, which in turn secures the upstream stator 160 by pressing against the stator blades 164. In addition to providing a radial inward force for securing the upstream stator 160, the sealing elements 172 can hermetically seal the plug holes 173 by, for example, expanding slightly when pressed against the tubular portion 127b. The sealing elements 172 can be made from any fluid-impermeable material and can be in the form of, for example, spherical plugs. Alternatively, the sealing elements 172 can have cylindrical, hemispherical, or other geometries.

Referring to FIG. 8C, a ratchet mechanism limits rotational movement of an inlet cap 302 relative to the stator cover 129. The ratchet mechanism includes limiting elements 312 that engage inner grooves 330 defined in the inner circumference of the inlet cap 302. The limiting elements 312 are partially disposed in radial holes 308 defined in the stator cover 129. Unlike the plug holes 173, the radial holes 308 extend only partially through the stator cover 129. Resilient elements 310, such as o-rings, are disposed in the holes 308 between the limiting elements 312 and the stator cover 129. The resilient elements 310 position the limiting elements 312 such that the limiting elements 312 protrude out of the holes 308. The resilient elements 310 also act as springs to counteract the radial force exerted by the inlet cap 302 so that the limiting elements 312 are frictionally engaged with the inlet cap 302. Thus, when the inlet cap 302 is connected to the stator cover 129, the limiting elements 312 enter and situate in the grooves 330. The resilient elements 310 exert a radial outward force on the limiting elements to limit rotation of the inlet cap 302 relative to the stator cover 129. In one implementation, the inlet cap 302 is threadedly screwed onto the stator cover 129. The combination of the grooves 330 and the limiting and resilient elements 312, 310 help to provide additional friction so that the inlet cap 302 cannot be easily unscrewed. Each limiting element 312 can be a spherical structure, or can have another other shape with a curved exposed surface that can engage with the grooves 330. Alternately, the combination of limiting and resilient elements can be replaced by a spring-loaded plug with a protruding element for engaging with the grooves. Instead of grooves 330 with a curved surface, the inner surface of the inlet cap 302 may have a saw-like or other configuration that generates friction to prevent the inlet cap 302 from coming loose.

Figure 9:
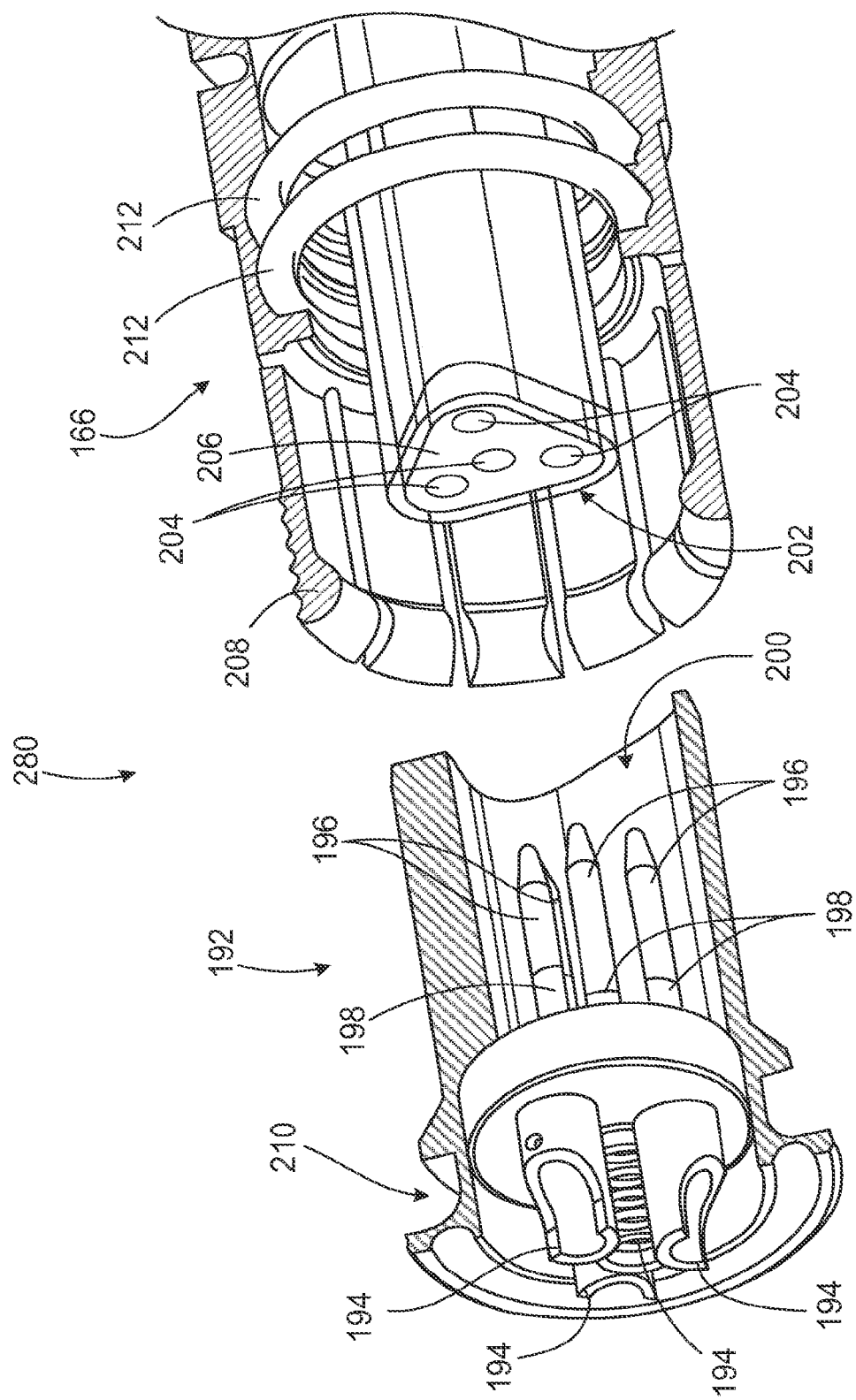
FIG. 9 is a cutaway perspective view of a connector for a driveline of a blood pump.

Referring to FIG. 9, a connector 280 that can be used with the pump 100 is shown. The percutaneous lead 118 described above has two ends, one end that is coupled with the pump 100 and another end that couples directly or indirectly to a control system and/or power source. The connector 280 shown in FIG. 9 can be configured for use at either end or both ends of the percutaneous lead 118. Further, the female portion (e.g., portion 192 of the connector 280) and male portion (e.g., portion 166 of the connector 280) can be used interchangeably on any end of the percutaneous lead 118, in the pump 100, or on a control system and/or power source. For example, the percutaneous lead 118 terminates in a power lead 166 (e.g., female portion) that attaches to a corresponding power end connector 192 (e.g., male portion) located within the port 122 of the housing 102 (FIG. 4). The power end connector 192 encloses a plurality of conductors 194 that terminate in pins 196. An insulation sleeve 198 fits over the conductors 194 to create a hermetic seal around the pins 196. The power end connector 192 can be formed as part of the housing 102 or can be formed separately and attached to the housing 102 by, for example, snap fit. A mating region 200 contains the pins 196 and is hermetically isolated from the inner portions of the housing 102.

The power lead 166 encloses multiple conductors 218a, 218b, 218c, 220 (FIG. 10) and can mechanically and electrically connect with the power end connector 192. The conductors 218a, 218b, 218c, 220 extend through the percutaneous lead 118 to connect phase windings of the motor stator 146 to a pump controller 216 (FIG. 10), as described further below. The power lead 166 has a power lead mating region 202 that defines a plurality of openings 204 for receiving and electrically connecting to the pins 196, and each opening 204 electrically connects to one of the conductors 218a, 218b, 218c, 220. The openings 204 of the power lead 166 can be formed within a seal wiper 206 that can provide pin-to-pin isolation for making connections in a wet environment. Alternatively, the pin and opening configuration can be reversed. For example, the mating region 200 can contain openings 204 formed with a seal wiper 206, and the power lead mating region 202 can contain a plurality of pins 196 surrounded by the insulation sleeve 198.

The pins 196 and the corresponding openings 204 of the mating regions 200, 202 can be arranged in an equilateral triangular pattern. When there are three pins 196 and three openings 204, for example, each pin 196 and opening 204 can be placed at a vertex of an equilateral triangle. With the mating regions 200, 202 arranged in an equilateral triangular pattern, and with the windings of the motor stator 146 arranged in a 120 degree three-phase configuration, the relative rotational orientation of the two mating regions 200, 202 does not affect motor performance, as only the relative order of electrical connections needs to remain consistent.

In some implementations, a fourth pin 196 is included in the power end connector 192 and a fourth opening 204 is defined in the mating region 202. The fourth pin 196 and fourth opening 204 can be placed at the center of the triangular pattern, with the remaining pins 196 and openings 204 located at the vertices of the triangle, as described above. When the fourth pin 196 and opening 204 are connected to a common conductor of the three-phase motor, such as the additional conductor 220 as described further below, the rotational orientation of the two mating regions 200, 202 relative to each other will not affect motor performance. As a result, a surgeon can easily connect the power lead 166 to the power end connector 192 using an alignment in any of three positions.

Mechanical latching between the power lead 166 and the power end connector 192 can be achieved through tabs or tines 208 disposed circumferentially around the power lead 166 that snap into a groove 210 disposed circumferentially around the power end connector 192. Alternatively, the mechanical latching features can be reversed. After the tines 208 couple to the groove 210, an outer sleeve (not shown) slidably positioned over the power lead 166 can slide over the tines 208 to prevent the tines 208 from moving out of the groove 210.

When the connector 280 is implanted into a patient, it must hermetically isolate the contacts from fluids in the body while providing appropriate pin to pin orientation and create a secure mechanical connection. Using a triangular clocking feature allows the connector 280 to be inserted at three different orientations 120 degrees apart. There is no concern for having a connection in a particular orientation because the connection is made to a three-phase motor. In other words, different orientations of connection are acceptable. As long as the phases are connected in the same order to the cable wires, the specific wire-to-wire connection is not important. Therefore, when the connector 280 is connected at each of the three different orientations, the order of the phases is not changed even though the individual wire-to-wire connections change. Typically connectors use a single clocking position so depending on the starting orientation, the connector must be rotated up to 360 degrees before the connection can be made. The triangular connector requires at most a 120 degree rotation to insert the connector. This facilitates the ease of use and reduces any potential twisting of the cable as a result of the connection. If redundant connection pins for each phase are desired a similar triangular clocking can be accomplished by positioning 6 pins in an equilateral triangular pattern. Alternate wiring approaches can also be configured with the triangular keying. One example of this is for a 4 conductor connection involving a three phase motor (described below). For this case the phases are kept in the triangular pattern and the fourth connection is made through a central pin. In this case only the motor phase pins change with the different clocking and the central connection remains the same.

Figure 10:
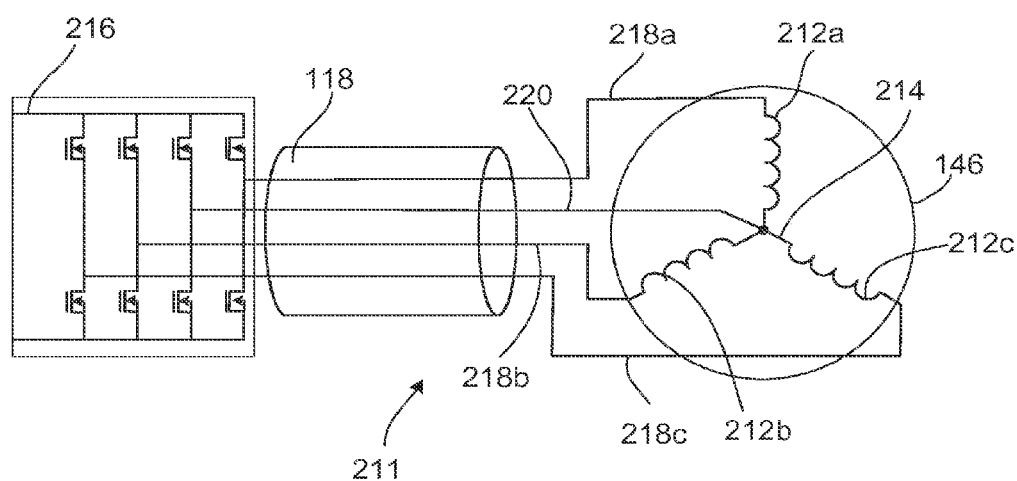
FIG. 10 is a schematic diagram that illustrates a drive system for a blood pump.

Referring to FIG. 10, a motor drive system 211 includes phase windings for at least three phases. For example, the motor drive system 211 has a three-phase configuration for the motor stator 146 and has three phase windings 212a, 212b, 212c that are placed 120 degrees apart about the inlet axis 120. Each of the phase windings 212a, 212b, 212c has a first end and a second end, and the second end of each phase winding 212a, 212b, 212c is connected to a common loadable point 214. The three windings 212a, 212b, 212c and are separately connected to a controller 216 through the three conductors 218a, 218b, 218c. Additionally, the common loadable point 214 is connected to the controller 216 through an additional conductor 220. The additional conductor 220 can be a neutral connection but can also be driven independently through independent drive electronics.

The percutaneous lead 118 includes the set of conductors 218a, 218b, 218c, 220, including the first conductor 218a for connecting the pump controller 216 and the first end of the first phase winding 212a, the second conductor 218b for connecting the pump controller 216 and the first end of the second phase winding 212b, and the third conductor 218c for connecting the pump controller 216 and the first end of the third phase winding 212c. The set of conductors includes an additional conductor 220 for connecting the pump controller 216 and the common loadable point 214.

The pump controller 216 is configured to independently control current in the first conductor 218a, the second conductor 218b, the third conductor 218c, and the additional conductor 220. For example, the controller 216 contains independent drive electronics for each of the three windings 212a, 212b, 212c and for the additional conductor 220 and thus can independently control each phase of the motor stator winding. Because the additional conductor 220 can be driven independently of the conductors 218a, 218b, 218c, the motor drive system 211 can be operated as a three-phase, two-phase, or a one-phase system. As a result, the pump 100 can be operated even when faults are present in the drive electronics, the phase windings 212a, 212b, 212c, and the conductors 218a, 218b, 218c, 220. For example, if a fault disconnects one of the phase windings 212a, 212b, 212c, the motor drive system 211 can detect this fault condition then switch to a two-phase operation mode. Similarly, if two of the phase windings 212a, 212b, 212c become disconnected, the motor drive system 211 can be operated in a one-phase mode. As another example, if the connection through the additional conductor 220 is broken, the motor drive system 211 can be operated in three-phase mode. Finally, if a fault occurs in the additional conductor 220 and a fault occurs in one of the phase windings 212a, the motor drive system 211 can be operated in single-phase mode.

Figure 11:
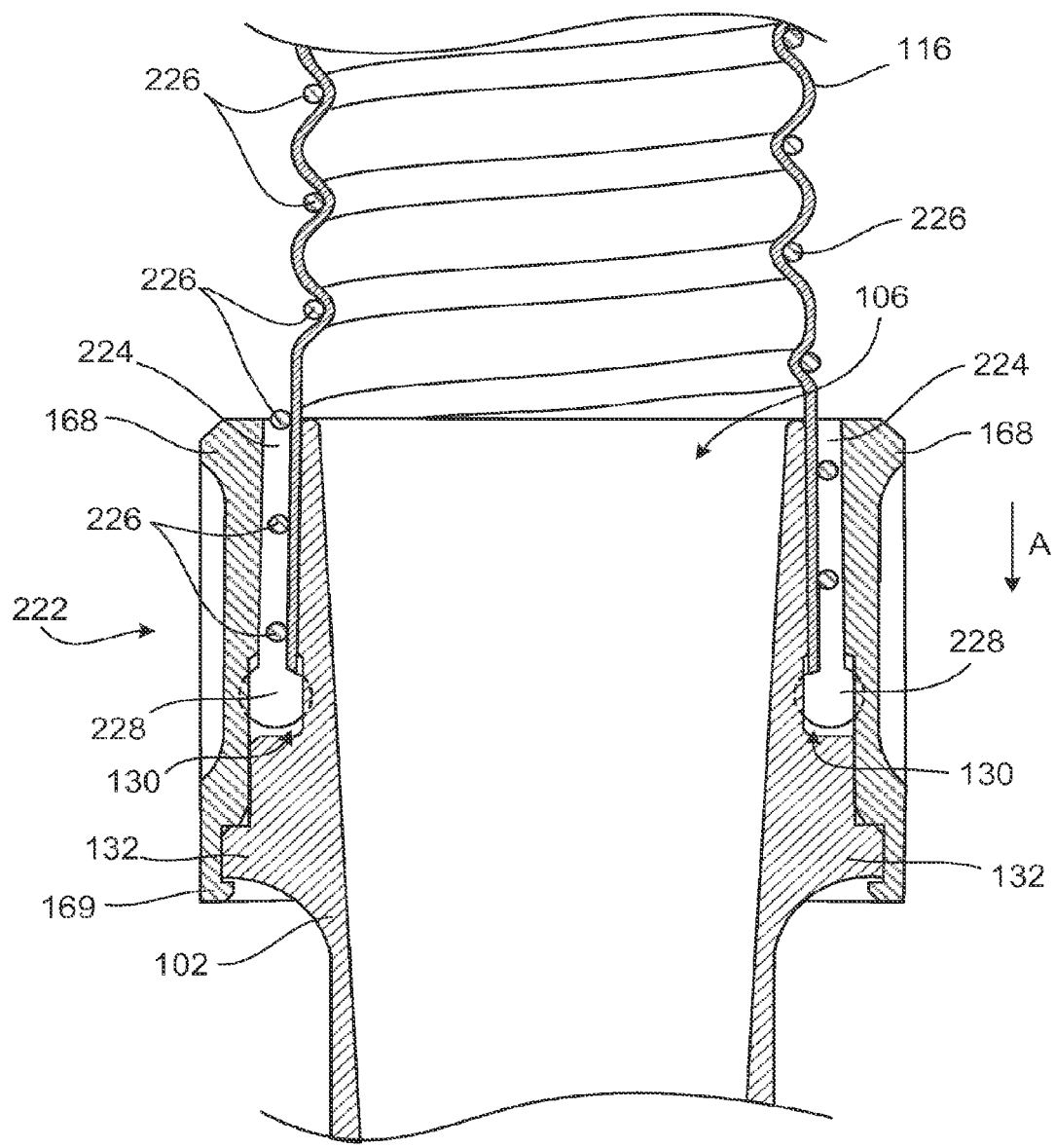
FIG. 11 is a cutaway view of a graft assembly.

FIG. 11 illustrates a graft assembly 222 for use with pump 100. The graft assembly 222 provides fluid communication from the outlet 106 of the pump 100 to a target vasculature, vessel, or organ in the circulatory system. The graft assembly 222 includes a conduit 116 that defines a lumen 225, a reinforcement component 226 about the conduit 116, and a support structure 224 molded about the conduit 116.

The conduit 116 can be formed of, for example, a woven material, for permitting the conduit 116 to be sewn to, for example, a blood vessel. The material of the conduit can be a non-synthetic or synthetic material, including, but not limited to polytetrafluoroethylene (PTFE) and polyester fabric (e.g., Dacron). The reinforcement component 226, such as a polymer monofilament or a wire, is helically wrapped about the conduit 116 to provide the conduit 116 with additional strength and to prevent kinking of the conduit when in use. The conduit 116 has inherent resiliency such that it can return its standard or neutral shape after being twisted or subjected to a compression force. In some implementations, every region the graft assembly 222 incorporates a slightly elastic or resilient property to resist kinking and compression. The support structure 224 is molded about an end region 117 of the conduit 116. The support structure 224 may be rigid or flexible, but it is designed to anchor the conduit 116 over the external housing of the pump 100 or at the outlet 106 of the pump 100. The reinforcement component 226 can be embedded within the support structure 224. The support structure 224 has a lip or a flange 228 at an end that extends about the conduit 116 and laterally inward and outward from the conduit 116 to provide anchoring. The flange 228 can enhance the sealing of the connection between the graft assembly 222 and the pump 100 as described further below.

In some implementations, the graft assembly 222 can engage exterior housing features of the pump 100 to attach and seal around the outlet 106. Proximate the outlet 106, the exterior of the housing 102 includes a recessed portion 130 and a raised portion 132 that extend partially or completely about the outlet 106. The conduit 116 can slide over the outlet 106 in the direction of arrow A until the flange 228 reaches the recessed portion 130 and the support structure 224 engages the raised portion 132, limiting further motion toward the pump 100. To secure the conduit 116 to the housing 102, the fitting 168 can be, for example, pulled over the molded support structure 224 in the direction of arrow A such that a portion 169 of the fitting 168 snaps over and couples with the raised portion 132 of the outlet 106. As the fitting 168 slides over the support structure 224, the fitting 168 compresses the flange 228 into the recessed portion 130, forming a seal around the outlet 106. In some cases, the recessed portion 130 can be omitted.

In some implementations, an inner portion of the fitting 168 can be threaded to engage external threads (not shown) of the housing 102 that are located about the outlet 106. Screwing the fitting over the support structure 224 and the external threads compresses the flange 228 to form a seal about the outlet 106. In some implementations, the fitting 168 is formed of two semi-cylindrical pieces that fit over the conduit 116 and a portion of the housing 102 to capture the support structure 224 and compress the flange 228 to form a seal. The two semi-cylindrical pieces can attach to each other via, for example, set screws.

In some implementations, the lumen of the conduit 116 has a same diameter as the edge of opening of the outlet 106. Generally, the conduit of the lumen has the same diameter as the opening of the outlet 106. Thus the outflow blood path would have a similar diameter from a region proximate the downstream bearing assembly through the conduit if the outlet 106 has a same diameter from a region proximate the downstream bearing assembly to the opening. But the outflow can also have a funnel or tapered lumen where if the opening of the outflow has a larger diameter relative to the region proximate the downstream bearing assembly.

Figure 12A:
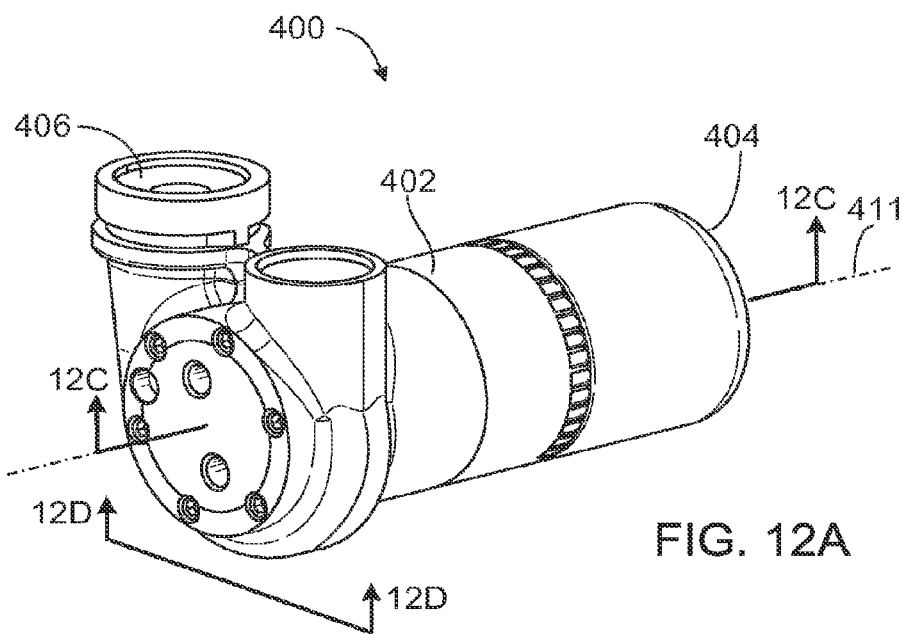
FIG. 12A is a perspective view of an alternative blood pump.
Figure 12B:
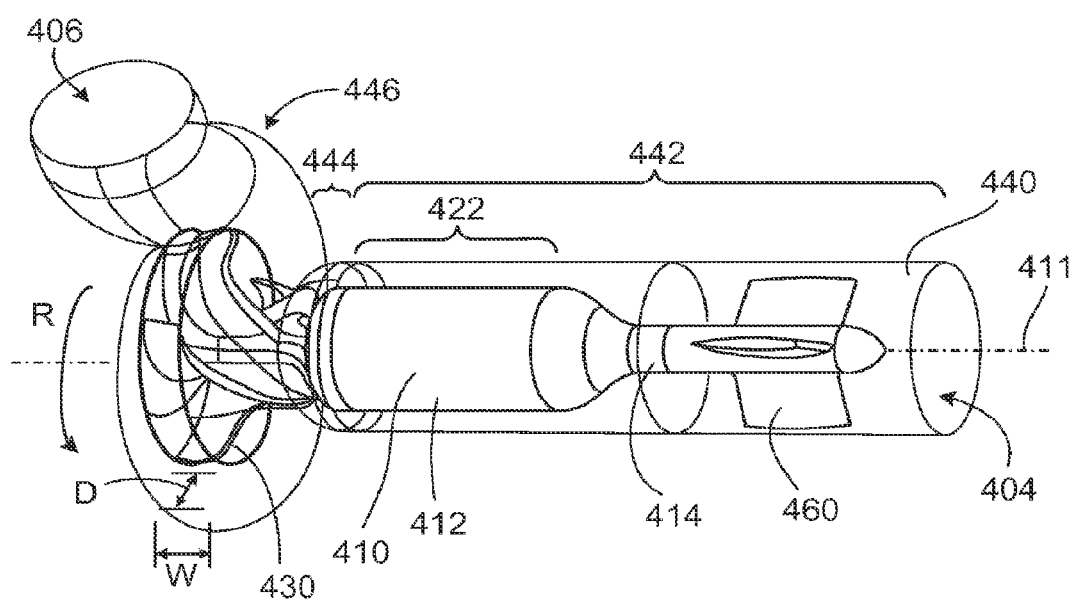
FIG. 12B is a diagram illustrating a rotor and fluid flow path of the blood pump of FIG. 12A.

Referring to FIGS. 12A and 12B, an alternative blood pump 400 includes an alternative rotor 410. The rotor 410 rotates around an axis 411, for example, in a counter clockwise direction, R, creating axial and radial (e.g., centrifugal) flows within a flow path 440 (FIG. 12B). The rotor 410 is located in a housing 402 that has the same types of components as the housing 102 of the blood pump 100 (see FIGS. 2, 3A, 3B, and 4). However, the housing 402 accommodates a rotor 410 different from the rotor 133 and the housing 402 defines a flow path 440 that is modified relative to the flow path 108.

In the flow path 440, fluid enters an inlet 404 and exits through an outlet 406. Between the inlet 404 and the outlet 406, the flow path 440 includes a channel 442, a tapered region 444, and a volute 446. The channel 442 is generally cylindrical and surrounds an upstream stator 460 and upstream portions of the rotor 410. In some implementations, the channel 442 has a substantially constant diameter that extends from the upstream stator 460 along at least half of the rotor 410. The diameter of the flow path 440 then decreases in the tapered region 444, which is located around a downstream end of the rotor 410. In some implementations, the narrowest outer diameter of the flow path 440 along the axis 411 occurs at the end of the tapered region 444. The volute 446 is located downstream of the tapered region 444.

Figure 12C:
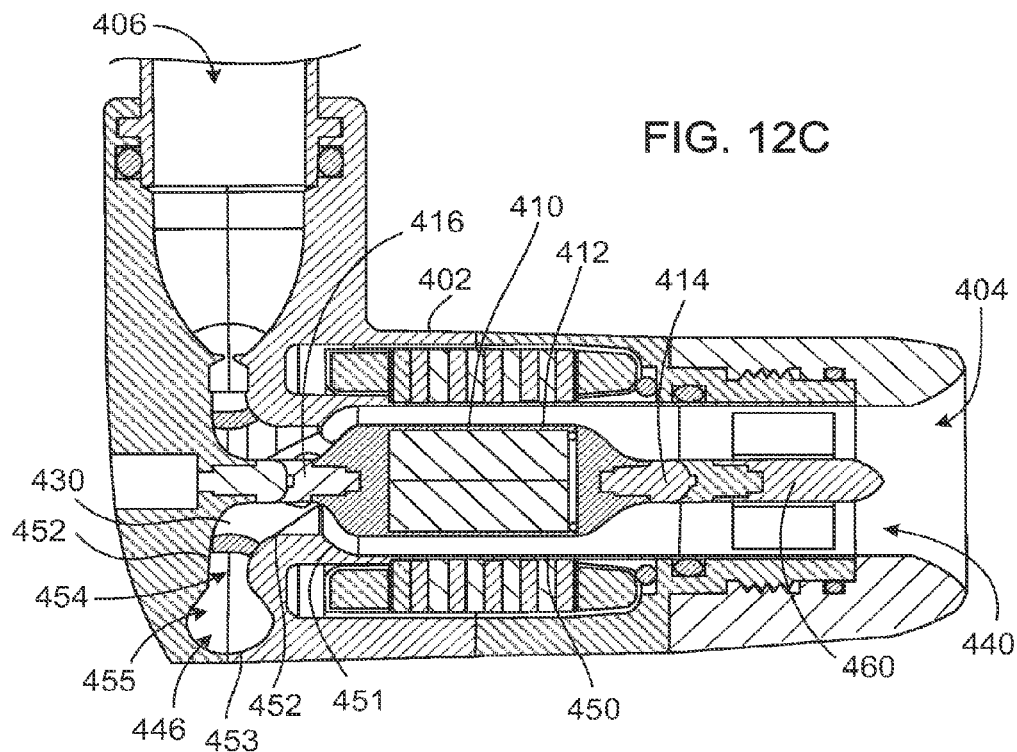
FIGS. 12C and 12D are cross-sectional views of the blood pump of FIG. 12A.

Referring to FIG. 12C, the housing 402 defines the flow path 440 with inner walls 450, 451, 452, 453. A cylindrical inner wall 450 defines the channel 442, and inward flaring wall 451 decreases the diameter of the flow path 440 in the tapered region 444. Circumferential walls 452 define an annular channel leading to the volute 446, providing a desired amount of clearance between the outer edges of the blades 430. In some implementations, the walls 452 are dimensioned to provide a consistent clearance around the blades 430 except at a free end of each blade 430 that extends into the volute 446. Walls 453 define the volute 446, including an outer ring 455 that has expanding cross-sectional area along the direction of rotation, R.

Figure 12D:
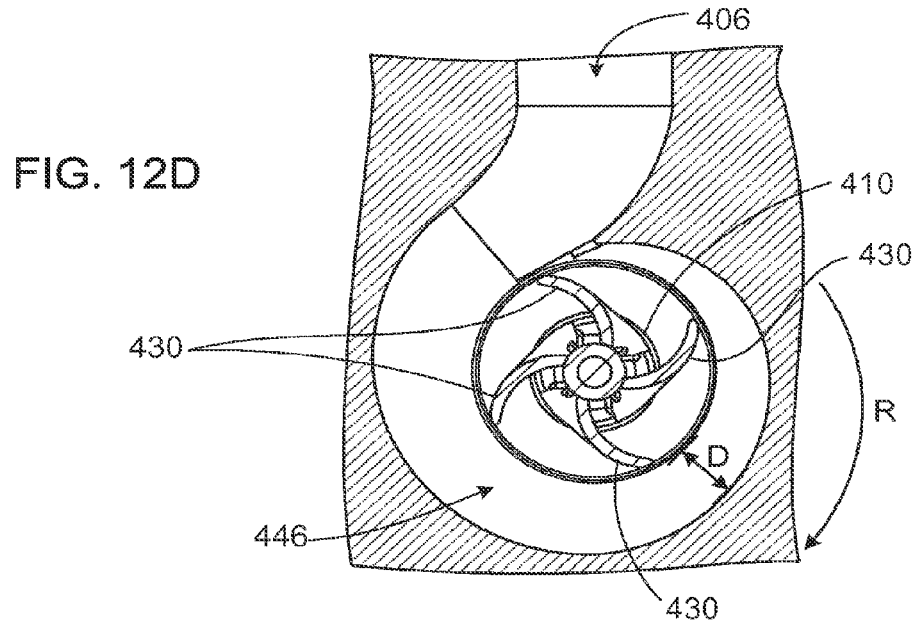

Referring to FIG. 12D, in some implementations, the volute 446 includes a spiral region that extends around the axis 411, centered on (e.g., located generally symmetrically about) a plane generally perpendicular the axis 411. The volute 446 expands along the direction of rotation, R, providing an increasing distance, D, from the end of blades 430 on the rotor 410 and an increasing width, W, measured parallel to the axis 411 (see FIG. 12B).

Figure 13A:
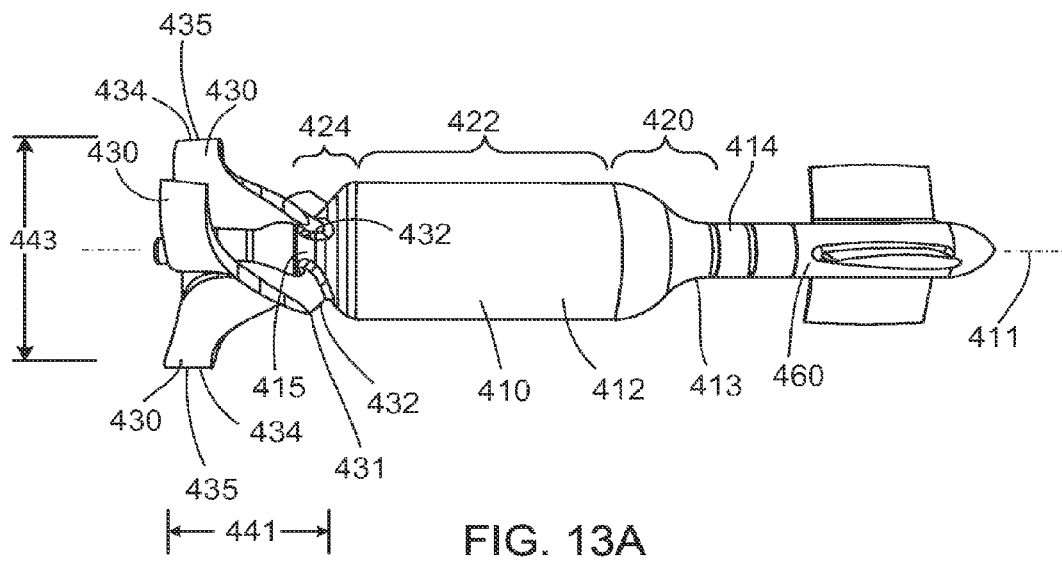
FIG. 13A is a side view of a rotor and bearing assembly of the blood pump of FIG. 12A.

Referring to FIG. 13A, the rotor 410 includes a hub 412, an upstream bearing component 414, and a downstream bearing component 416. The outer diameter of the upstream bearing component 414 and the downstream bearing component 416 are approximately equal. Between the bearing components 414, 416, viewed along in the direction of the fluid flow, F, the hub 412 increases to a maximum outer diameter, remains constant at the maximum outer diameter in a central region 422, and then decreases.

In further detail, the hub 412 includes a tapered region 420 at a fore or proximal end 413 of the hub 412, adjacent the upstream bearing component 414. In the tapered region 420, the outer diameter of the hub 412 increases gradually to reach a maximum outer diameter of the hub 412. Adjacent the tapered region 420, the hub 412 includes the central region 422, in which the outer diameter of the hub 412 is cylindrical or substantially constant. Adjacent the central region 422, the hub 412 also includes a tapered region 424 at an aft or distal end 415 of the hub 412 in which the outer diameter of the hub 412 decreases from the maximum outer diameter of the hub 412 to the outer diameter of the downstream bearing component 416. In some implementations, the change in diameter of the hub 412 occurs more steeply in the tapered region 424 than in the tapered region 420. For example, the tapered region 424 may be two thirds or less of the length of the tapered region 420 along the axis 411.

The rotor 410 includes four blades 430, which extend from the tapered region 424 at the distal end 415 of the hub 412. The blades 430 are spaced apart equally around the circumference of the hub 412, for example, approximately 90 degrees apart around the axis 411. Each blade 430 includes a fixed end 432 that is anchored to the hub 412 in the decreasing tapered region 424, for example, at an aft-facing surface 425 of the hub 412. In this regard, the blades 430 connect differently from the blades 142 of the rotor 133, since the blades 142 extend from the hub 134 from a connection at the largest outer diameter of the hub 134 (see FIG. 5A). The connection of the forward leading edge of exemplary blade 430 at the aft-facing surface 425 is the only connection between the blade 430 and the rotor 410. In some implementations, the blades 430 connect to the aft-facing surface 425 at an inflection region where the aft-facing surface 425 transitions from an increasing rate of change of the outer diameter of the hub 412 to a decreasing rate of change of the outer diameter of the hub 412.

Each blade 430 cantilevers or projects from the hub 412 and terminates in a free end 434 that extends into the volute 446. The free end 434 can include a generally linear trailing edge that extends in a direction that is substantially parallel to the axis 411. Each blade 430 extends distally beyond the distal end 415 of the hub 412 and past the downstream bearing component 416, with each blade 430 twisting along its length. No blades are disposed on or are located around the tapered region 420 or the central region 422 of the hub 412. Each blade 430 extends circumferentially around the axis 411 by approximately 90 to 110 degrees.

Each blade 430 includes an inner edge 445 that has a portion that faces generally inward toward the axis 411 and a portion that faces generally in an aft direction. Each blade 430 also includes an outer edge 448 that has a portion that faces generally outward toward the walls 451, 452 of the pump housing 402, having a portion that faces generally outward from the axis 411 and a portion that faces generally forward, toward the inlet 404.

Each blade 430 includes, at the fixed end 432, a leading edge 431 that is angled with respect to the axis 411. For example, the leading edge 431 can extend linearly at an angle between approximately 30 degrees and approximately 60 degrees, or at an angle of 45 degrees. In some implementations, the leading edge 431 terminates at a distance from the axis 411 that is approximately equal to the maximum outer diameter of the hub 412. The distance that the leading edge 431 extends may vary according to the amount of space provided by the inner walls 451,452 of the housing 402.

Figure 13B:
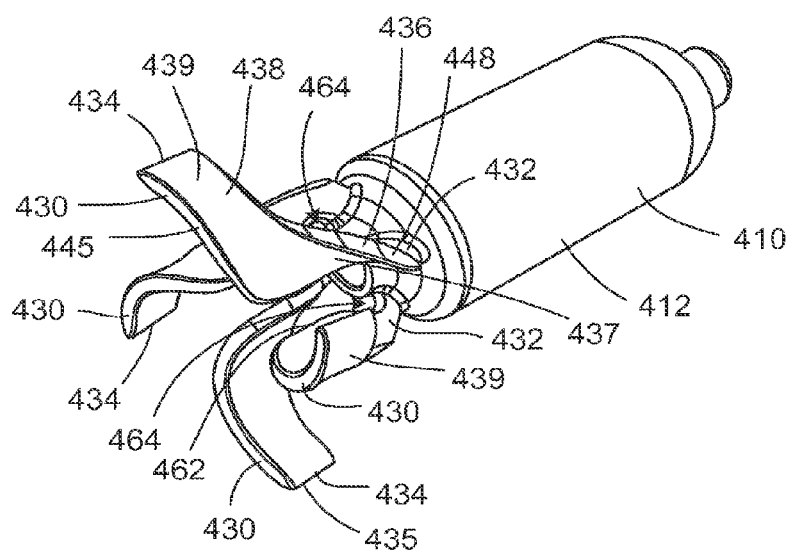
FIG. 13B is a perspective view of the rotor of the blood pump of FIG. 12A.

Referring to FIG. 13B, the rotor 410 is shown without the bearing components 414, 416 that are carried by the rotor 410. Each blade 430 has a leading portion or upstream portion 436 proximate the hub 412 that includes a concave surface 437 that imparts energy to fluid flowing in the axial direction. Each blade 430 also includes a downstream region 438 that includes a convex surface 439 that imparts energy to the flow flowing in primarily a radially outward or centrifugal direction. The downstream region 438 is generally surrounded by the volute 446. Fluid drawn axially by the concave surface 437 is accelerated and flung outward along the convex surface 439 into the volute 446.

Each blade 430 includes an inner edge that faces toward the axis 411. The inner edge 462 defines a notch or concave gap 464, or other region that curves away from the axis 411. The concave gap 464 can be located over or upstream of the downstream bearing component 416. The concave gap 464 increases flow to promote washing of the downstream bearing. In some implementations, the narrowest portion of the face of the blade 430 occurs at the location of the concave gap 464.

The blades 430 of the rotor 410 project generally radially outward from the hub or axis of rotation. As shown in FIG. 13A, for example, the radial length of each blade 430 is significantly greater than the axial length of the blade 430. By contrast, the blades 142 of exemplary rotor 133 have a generally longer axial length. In various embodiments, an axial length 441 of the blade section is greater than the diameter 443 of the blade section. In other words, the blades 430 may be shaped and configured to project distally in a fin-like configuration. In various embodiments, the axial length 441 of the blade section is less than the diameter 443 of the blade section. In the exemplary embodiment of FIG. 13A, the leading edge 431 extends from the aft of the hub 412 in an axial direction. The trailing edge 435 has a chamfer shape at its start point and thereafter generally extends in a predominantly radial direction.

Figure 13C:
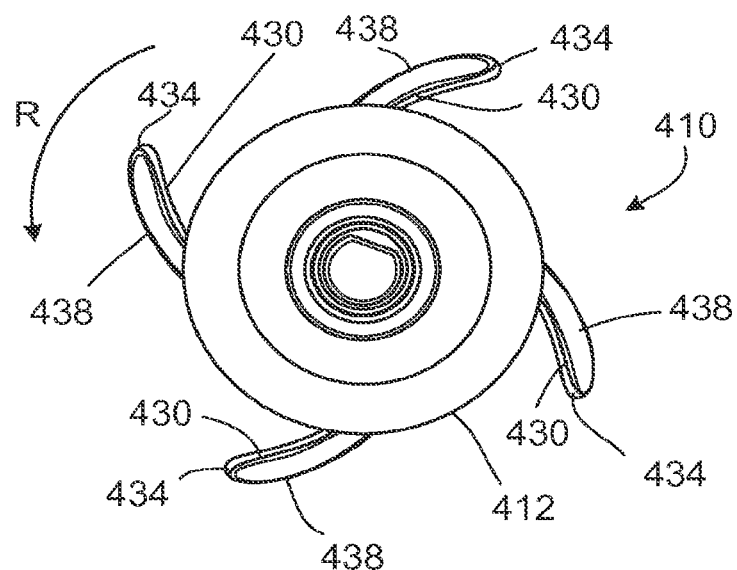
FIG. 13C is a front view of the rotor of FIG. 13B.
Figure 13D:
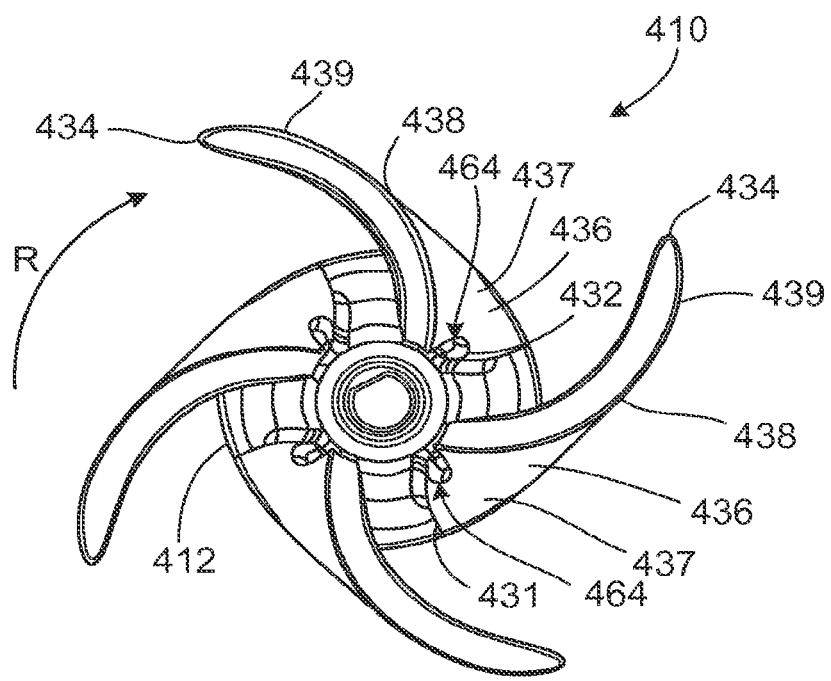
FIG. 13D is a back view of the rotor of FIG. 13B.

Referring to FIGS. 13C and 13D, when the rotor 410 is viewed along the axis 411, the profile of the hub 412 covers the upstream portion 436 of each blade 430, which includes the fixed ends 432 of the blades 430 and substantially all of the twisting along the blades 430. Thus the axial flow components imparted by the blades 430 are generated in a cylindrical region with an outer diameter no greater than the outer diameter of the hub 412. The upstream portions 436 of the blades 430 are located in a narrowed region of the flow path 440, for example, after the inner diameter of the housing 402 decreases along the walls 451, which may be the narrowest inner diameter about the axis 411. As a result, fluid flow to the upstream portions 436 can have a higher velocity than fluid flow through upstream regions of the flow path 440. The higher velocity in this narrowed flow region, together with the rotation of the leading portions of the blades, can provide strong washing currents. This region can be located over the downstream bearing component 416 and other downstream bearing components (see FIG. 12C) to reduce the risk of thrombogenesis. The downstream regions 438 extend radially outward from the axis 411 beyond the maximum outer diameter of the hub 412. The downstream regions 438 are aligned substantially parallel to the axis 411.

In some implementations, axial fluid flow along the rotor 410 is substantially constant when the pump 400 is in operation. Blood has a very low compressibility, and may be considered incompressible. Where no energy is added to the flow, and energy in the flow remains generally constant, velocity of the flow tends to be inversely proportional to pressure upstream of the blades 430 due to changes in the outer diameter of the flow path 440. Generally, the tapered region 444 of the flow path 440, in which the flow channel narrows over the downstream end of the hub 412 (e.g., over the tapered region 424 of the hub 412), is intended to increase velocity of the flow. While this initially results in head loss (e.g., a lower pressure), the decrease in pressure in the tapered region 444 is localized and relatively small. Further, the effect of the localized decrease in pressure is reduced because the tapered region 444 occurs proximate (e.g., adjacent to) the blades 430. The blades 430 impart energy to the fluid and thus increase pressure. For example, in the region of the flow path 440 in which the blades 430 are disposed, the blades 430 move the fluid from one point to another, imparting kinetic energy which increases pressure.

Figure 14A:
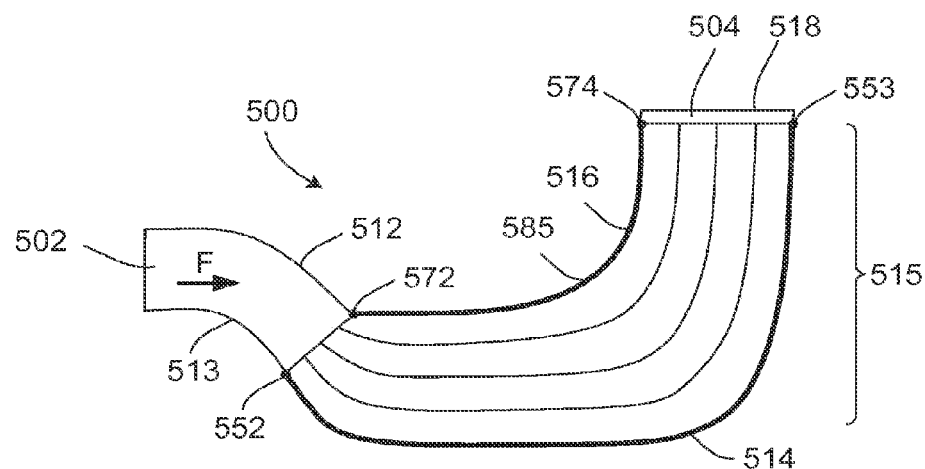
FIG. 14A is a meridional view of an example of a blade.

Referring to FIG. 14A, a meridional view of an example of a blade 500 is shown. For example, the view represents features along a path defined by an axisymmetric stream surface through the center of the blade 500.

The blade 500 may be disposed on a hub and positioned within a housing as described above. The blade 500 has the same general shape as the blade 430 described above. Flow over the blade 500 occurs in the general direction of arrow F. The blade 500 has a fixed end 502 disposed on the hub, and a free end 504 that extends toward a volute. In some implementations, the free end 504 extends to or into the volute. The fixed end 502 can be formed as strut or other feature, and includes a leading edge 512 and a rear edge 513.

The blade 500 also has an inner edge 514, an outer edge 516, and a trailing edge 518. The inner edge 514 faces generally inward toward the axis of rotation of the hub, for example, facing in toward the axis of rotation and in an aft or downstream direction. The outer edge 516 faces generally outward from the axis of rotation, for example, having regions that face outward toward inner walls of the pump housing that define the flow path. In some implementations, the pump housing defines a shroud or sheath circumferentially around the outer edge 516, defining a desired clearance around the outer edge 516. An aft wall of the pump housing may define clearance with a generally aft-facing portion 515 of the inner edge 514. The trailing edge 518 faces and/or enters the volute, is generally linear, and may be chamfered or tapered. Due to twisting of the blade 500 along its length, the wrap angles and blade angles defined by the blade 500 are different at the inner edge 514 and outer edge 516, as described below.

Figure 14B:
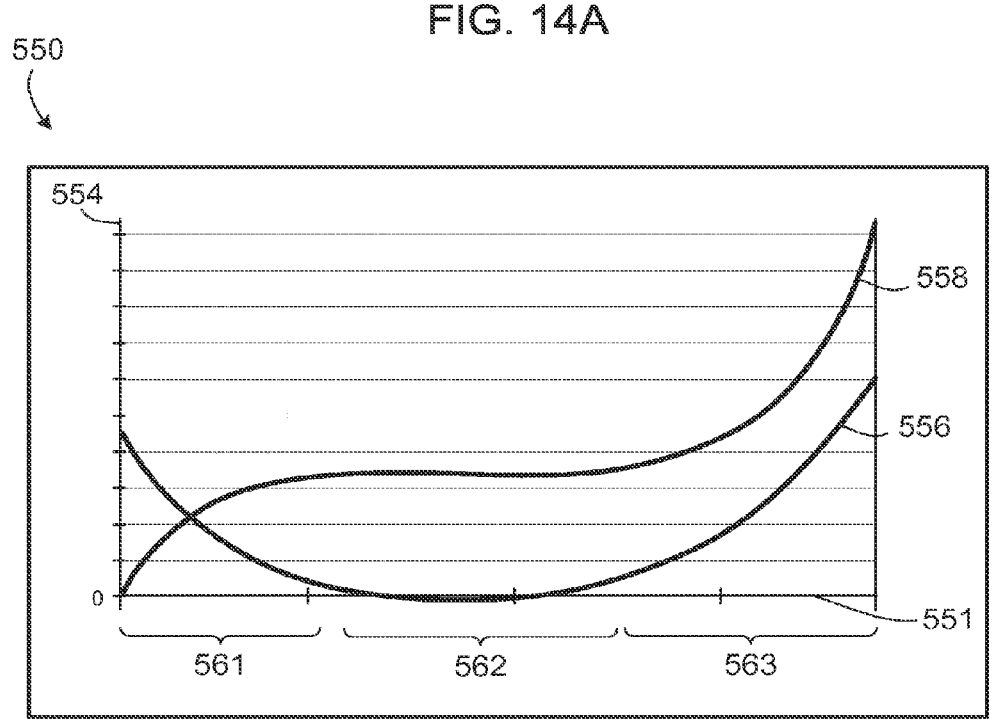
FIG. 14B is a graph illustrating characteristics of an inner edge the blade of FIG. 14A.

Referring to FIG. 14B, a graph 550 illustrates characteristics of the blade 500 along the inner edge 514. A blade angle curve 556 indicates changes of the blade angle along the inner edge 514, and a wrap angle curve 558 indicates the extent that the blade 500 extends circumferentially about the axis of rotation along the inner edge 514.

The horizontal axis 551 of the graph 550 indicates a normalized distance along the inner edge 514. The left side of the graph 550 represents the beginning of the inner edge 514, at position 552 in FIG. 14A, for example, adjacent the rear edge 513. The right side of the graph 550 represents the end of the inner edge 514, at position 553 of FIG. 14A, for example, adjacent the trailing edge 518. The vertical axis 554 indicates angle values, beginning at zero degrees and increasing up the vertical axis 554.

The wrap angle is defined as an angle that the blade 500 extends circumferentially around the axis of rotation. As indicated by the wrap angle curve 558, the wrap angle is defined to be zero degrees at the position 552, which is beginning or leading point of the inner edge 514. Along an initial region 561, which can be approximately the initial one quarter to one third of the length of the inner edge 514, the wrap angle increases. The wrap angle has a decreasing rate of change in the initial region 561. Along a central region 562, which can be approximately the central one third of length of the inner edge 514, the wrap angle remains generally constant. For example, the wrap angle varies within a range of 10 degrees, or within a range of 5 degrees, or less along the central region. Along an end region 563, which can be approximately the final one third of the length of the inner edge 514, the wrap angle increases with an increasing rate of change. In some implementations, the maximum wrap angle is approximately 100 degrees at the position 553 at the trailing edge 518 (indicated at the right edge of the graph 550). For example, the maximum wrap angle may be between 85 degrees and 115 degrees, or between 90 degrees and 110 degrees, etc. In some implementations, the magnitude of the rate of change of the slope of wrap angle curve 558 (e.g., the magnitude of the increase or decrease of the rate of change of the wrap angle) along the initial region 561 and along the end region 563 are approximately equal.

The blade angle is defined as an angle between the blade and the axis of rotation, represented on the graph 550 by the blade angle curve 556. From an initial blade angle value, the blade angle decreases along an initial portion of the inner edge 514, until approximately one third to one half of the length of the inner edge 514. Thereafter, the blade angle increases, ending at a blade angle equal to or greater than the initial blade angle. In some implementations, the blade angle curve 556 has a continuously increasing slope, indicating that the rate of change of the blade angle increases along substantially the entire inner edge 514. In some implementations, the rate of change of the blade angle (e.g., slope of the blade angle curve 556) increases at a generally constant rate.

In some implementations, the blade angle varies by at least 30 degrees, at least 40 degrees, at least 50 degrees, or more along the length of the inner edge 514. In some implementations, the lowest value of the blade angle along the inner edge 514 occurs at a position between approximately one third and one half of the length of the inner edge 514. In some implementations, the final blade angle along the inner edge 514 (e.g., at position 553, corresponding to the right side of the graph 550) is greater than the initial blade angle along the inner edge 514 (e.g., at position 552, corresponding to the left side of the graph 550). The final blade angle and the initial blade angle can be within approximately 30 degrees, 20 degrees, or 10 degrees of each other.

Figure 14C:
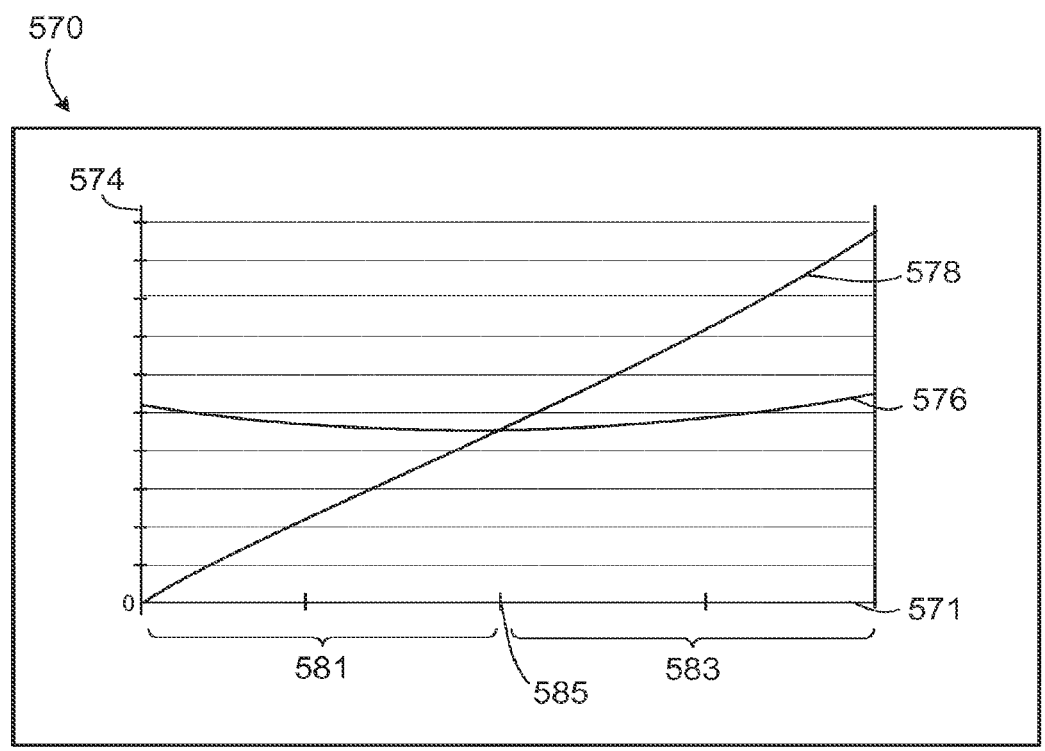
FIG. 14C is a graph illustrating characteristics of an outer edge of the blade of FIG. 14A.

Referring to FIG. 14C, a graph 570 illustrates characteristics of the blade 500 along the outer edge 516. A blade angle curve 576 indicates changes of the blade angle along the outer edge 516, and a wrap angle curve 578 indicates the extent that the blade 500 extends circumferentially about the axis of rotation along the outer edge 516.

The horizontal axis 571 of the graph 570 indicates a normalized distance along the outer edge 516. The left side of the graph 550 represents the beginning of the outer edge 516, at position 572 in FIG. 14A, for example, adjacent the leading edge 512. The right side of the graph 570 represents the end of the outer edge 516, at position 573 of FIG. 14A, for example, adjacent the trailing edge 518. The vertical axis 574 indicates angle values, beginning at zero degrees and increasing up the vertical axis 574.

The wrap angle is defined as an angle that the blade 500 extends circumferentially around the axis of rotation, as noted above. As indicated by the wrap angle curve 578, the wrap angle is defined to be zero degrees at the position 572, which is beginning or leading point of the outer edge 516. The wrap angle increases at a generally constant rate along the outer edge 516, indicated by the generally linear trajectory of the wrap angle curve 578. In some implementations, the final wrap angle (e.g., at the position 573) is approximately 100 degrees, for example, between 85 degrees and 115 degrees, or between 90 degrees and 110 degrees, etc.

The blade angle is defined as an angle between the blade and the axis of rotation, represented on the graph 570 by the blade angle curve 576. From an initial blade angle value, the blade angle decreases along an initial region 581 of the outer edge 516. The initial region 581 may be approximately the initial one third to one half of the length of the outer edge 516. The blade angle then increases along an end region 583 of the outer edge 516. The end region 583 can be approximately the final one third to one half of the length of the outer edge 516. In some implementations, the rate of change of the blade angle (e.g., slope of the blade angle curve 576) increases at a substantially constant rate along substantially the entire outer edge 516. In some implementations, the blade angle varies no more than approximately 20 degrees, or no more than approximately 10 degrees along the outer edge 516. In some implementations, the initial blade angle (e.g., at the position 572, corresponding to the left side of the graph 570) and the final blade angle along the outer edge 516 (e.g., at the position 573, corresponding to the right side of the graph 570) are approximately equal (e.g., within 10 degrees of each other, or within 5 degrees of each other). The lowest value of the blade angle along the outer edge 516 may occur at approximately the midpoint 585 along the length of the outer edge 516.

In some implementations, because the blades described above produce axial and radial (e.g., centrifugal) flows, the pumps described herein produce washing of downstream bearing components at lower flow rates than, for example, purely axial flow pumps. Appropriate washing at lower flow rates can be advantageous for lower levels of ventricular support, such as right ventricle support applications. Mixed axial and centrifugal flow may also reduce shear rate at surfaces within the pumps, reducing hemolysis. In addition, the flow characteristics may reduce fluid residence times within the pumps and reduce recirculation zones within the pumps, which may result in improved efficiency and reduced risk of thrombogenesis.

The foregoing descriptions of specific implementations of the present invention have been presented for purposes of illustration and description. They are not intended to be exhaustive or to limit the invention to the precise forms disclosed, and obviously many modifications and variations are possible in light of the above teaching. The implementations were chosen and described in order to best explain the principles of the invention and its practical application, to thereby enable others skilled in the art to best utilize the invention and various implementations with various modifications as are suited to the particular use contemplated. It is intended that the scope of the invention be defined by the claims appended hereto and their equivalents.

What is claimed is:

1. A blood pump assembly, comprising:
   an implantable blood pump;
   a power lead connected to the blood pump and enclosing at least four conductors, the power lead including a mating region that includes three connectors arranged in a triangular pattern and a fourth connector located at a center of the triangular pattern, each of the conductors terminating at one of the connectors; and
   a power connector including a mating region for connecting with the power lead mating region along an axis, the power connector mating region including four connectors each arranged to receive one of the power lead connectors,
   wherein the blood pump is configured to be powered by the power lead when the power lead and the power connector are connected in any one of three different rotational positions about the axis relative to one another.

2. The blood pump assembly of claim 1, wherein the connectors of either the power lead or the power connector comprise female connectors, and wherein the female connectors are formed within a seal wiper configured to make connections in a wet environment.

3. The blood pump assembly of claim 1, wherein the at least four connectors of the power lead comprise at least four pins, and the power connector comprises one or more insulation sleeves surrounding the at least four pins, the one or more insulation sleeves being configured to form a hermetic seal around the at least four pins.

4. The blood pump assembly of claim 1, wherein the power lead mating region comprises six connectors arranged in the triangular pattern and wherein the power connector mating region includes six connectors each arranged to receive one of the power lead connectors, and wherein half of the six connectors of the power lead are redundant connectors.

5. A blood pump assembly, comprising:
   an implantable blood pump;
   a power lead connected to the blood pump and enclosing at least four conductors, the power lead including a mating region that includes three connectors arranged in a triangular pattern and a fourth connector located at a center of the triangular pattern, each of the conductors terminating at one of the connectors; and
   a power connector including a mating region for connecting with the power lead mating region along an axis, the power connector mating region including four connectors each arranged to receive one of the power lead connectors,
   wherein the blood pump is configured to be powered by the power lead when the power lead and the power connector are connected in any one of three different rotational positions about the axis relative to one another,
   wherein the three conductors terminating at the three connectors arranged in the triangular pattern are each configured to connect to motor phase windings associated with the implantable blood pump, and
   wherein the conductor terminating at the connector at the center of the triangular pattern is configured to connect to a common loadable point associated with the motor phase windings.

6. A blood pump assembly, comprising:
   an implantable blood pump;
   a power lead connected to the blood pump and enclosing at least three conductors, the power lead including a mating region that includes three connectors arranged in a triangular pattern, each of the conductors terminating at one of the connectors; and
   a power connector including a mating region for connecting with the power lead mating region and an external surface extending circumferentially around the power connector, the power connector mating region including three connectors each arranged to receive one of the power lead connectors, wherein the external surface of the power connector defines an exterior groove circumferentially around the power connector,
   wherein the blood pump is configured to be powered by the power lead when the power lead and the power connector are connected in any one of three mating positions, and
   wherein the power lead comprises a plurality of tabs disposed circumferentially around the power lead, the tabs being configured to snap into the exterior groove to mechanically latch the power lead to the power connector thereby resisting disconnection thereof.

7. The blood pump assembly of claim 6, further comprising an outer sleeve slideably positioned over the power lead to prevent decoupling of the power lead and the power connector.

8. The blood pump assembly of claim 7, wherein the mating region of the power lead comprises a seal member configured to receive the connectors of the power connector and isolate the connectors of the power connector from each other when the connectors are received in the seal member, wherein the connectors of the power connector are configured to engage the connectors of the power lead within the seal member.

9. The blood pump assembly of claim 6, wherein the power lead is configured to engage the power connector along an axis, and the power lead is configured to electrically connect to the power connector when the power connector is oriented in any one of three different rotational positions about the axis relative to the power lead.

10. The blood pump assembly of claim 6, wherein the connectors of either the power lead or the power connector comprise female connectors, and wherein the female connectors are formed within a seal wiper configured to make connections in a wet environment.

11. The blood pump assembly of claim 6, wherein the at least three connectors of the power lead comprise at least three pins, and the power connector comprises one or more insulation sleeves surrounding the at least three pins, the one or more insulation sleeves being configured to form a hermetic seal around the at least three pins.

12. The blood pump assembly of claim 6, wherein the power lead connected to the blood pump encloses four conductors, the fourth conductor terminating at a fourth connector of the mounting region located at a center of the triangular pattern, and wherein the power end connector mating region includes a fourth connector for receiving the fourth power lead connector.

13. The blood pump assembly of claim 6, wherein the power lead mating region comprises six connectors arranged in the triangular pattern and wherein the power connector mating region includes six connectors each arranged to receive one of the power lead connectors, and wherein half of the six connectors of the power lead are redundant connectors.

* * * * *